(12) United States Patent
Cole et al.

(10) Patent No.: US 10,258,823 B2
(45) Date of Patent: Apr. 16, 2019

(54) INSTRUMENTED TOTAL BODY RECUMBENT CROSS TRAINER SYSTEM

(71) Applicant: NuStep, Inc., Ann Arbor, MI (US)

(72) Inventors: Neil M. Cole, Dexter, MI (US); Douglas R. Hennigar, Ann Arbor, MI (US); Richard N. Sarns, Ann Arbor, MI (US); Steven W. Sarns, Dexter, MI (US); Matthew P. Weber, Brighton, MI (US); Carol J. Wilson, Dexter, MI (US)

(73) Assignee: NUSTEP, INC., Ann Arbor, MI (US)

( * ) Notice: Subject to any disclaimer, the term of this patent is extended or adjusted under 35 U.S.C. 154(b) by 259 days.

(21) Appl. No.: 15/104,423

(22) PCT Filed: Jan. 26, 2015

(86) PCT No.: PCT/US2015/012837
§ 371 (c)(1),
(2) Date: Jun. 14, 2016

(87) PCT Pub. No.: WO2015/112945
PCT Pub. Date: Jul. 30, 2015

(65) Prior Publication Data
US 2016/0361597 A1    Dec. 15, 2016

Related U.S. Application Data

(60) Provisional application No. 61/931,099, filed on Jan. 24, 2014, provisional application No. 61/952,529, filed on Mar. 13, 2014.

(51) Int. Cl.
*A61B 5/00* (2006.01)
*A61B 5/024* (2006.01)
(Continued)

(52) U.S. Cl.
CPC ........ *A63B 24/0062* (2013.01); *A63B 22/001* (2013.01); *A63B 22/0056* (2013.01);
(Continued)

(58) Field of Classification Search
None
See application file for complete search history.

(56) References Cited

U.S. PATENT DOCUMENTS

| 5,356,356 A | 10/1994 | Hildebrandt et al. |
| 7,775,945 B2 | 8/2010 | Hildebrandt et al. |

(Continued)

OTHER PUBLICATIONS

International Search Report and Written Opinion dated May 5, 2015.

*Primary Examiner* — Sundhara M Ganesan
(74) *Attorney, Agent, or Firm* — Brinks Gilson & Lione

(57) ABSTRACT

A physical exercise device providing a stepper like motion for a user may include a pair of foot pedals and a pair of arms for engagement by the user while seated on the seat of the physical exercise device. The pair of foot pedals and the pair of arms may be connected to a drive train which provides contralateral motion between the pair of arms and the pair of foot pedals. A pedal and arm lock mechanism may also be provided which prevents the pedals and arms to be moved in a lock state, while allowing movement of the pedals and the arms when in the unlock state. The physical exercise device may also include computational and data acquisition units for receiving a position signal and pedal force signals and recording the signals.

43 Claims, 39 Drawing Sheets

(51) Int. Cl.

| | | |
|---|---|---|
| *A63B 21/00* | (2006.01) | |
| *A63B 21/22* | (2006.01) | |
| *A63B 22/00* | (2006.01) | |
| *A63B 22/06* | (2006.01) | |
| *A63B 23/04* | (2006.01) | |
| *A63B 24/00* | (2006.01) | |
| *A63B 69/00* | (2006.01) | |
| *A63B 71/00* | (2006.01) | |
| *A63B 71/06* | (2006.01) | |
| *A63B 21/002* | (2006.01) | |
| *A63B 21/005* | (2006.01) | |
| *A63B 21/015* | (2006.01) | |
| *A63F 13/245* | (2014.01) | |
| *A63F 13/816* | (2014.01) | |

(52) U.S. Cl.
CPC ...... *A63B 24/0075* (2013.01); *A63B 24/0087* (2013.01); *A63B 71/0619* (2013.01); *A63F 13/245* (2014.09); *A63F 13/816* (2014.09); *A61B 5/024* (2013.01); *A61B 5/6895* (2013.01); *A61B 2503/10* (2013.01); *A63B 21/0023* (2013.01); *A63B 21/0051* (2013.01); *A63B 21/015* (2013.01); *A63B 21/151* (2013.01); *A63B 21/154* (2013.01); *A63B 21/157* (2013.01); *A63B 21/225* (2013.01); *A63B 22/0012* (2013.01); *A63B 22/0664* (2013.01); *A63B 23/0429* (2013.01); *A63B 69/0048* (2013.01); *A63B 2024/0065* (2013.01); *A63B 2024/0068* (2013.01); *A63B 2024/0081* (2013.01); *A63B 2024/0096* (2013.01); *A63B 2071/0081* (2013.01); *A63B 2071/065* (2013.01); *A63B 2071/0627* (2013.01); *A63B 2071/0638* (2013.01); *A63B 2071/0652* (2013.01); *A63B 2208/0238* (2013.01); *A63B 2210/50* (2013.01); *A63B 2220/17* (2013.01); *A63B 2220/30* (2013.01); *A63B 2220/51* (2013.01); *A63B 2220/54* (2013.01); *A63B 2220/56* (2013.01); *A63B 2220/803* (2013.01); *A63B 2225/09* (2013.01); *A63B 2225/093* (2013.01); *A63B 2225/20* (2013.01); *A63B 2225/50* (2013.01); *A63B 2230/01* (2013.01); *A63B 2230/06* (2013.01); *A63B 2230/207* (2013.01); *A63B 2230/60* (2013.01)

(56) References Cited

U.S. PATENT DOCUMENTS

| | | | |
|---|---|---|---|
| 2006/0094569 A1 | 5/2006 | Day | |
| 2007/0123390 A1 | 5/2007 | Mathis | |
| 2011/0082010 A1 | 4/2011 | Dyer | |
| 2011/0082397 A1* | 4/2011 | Alberts | A61H 1/02 601/26 |
| 2013/0137550 A1 | 5/2013 | Skinner et al. | |
| 2014/0274564 A1* | 9/2014 | Greenbaum | A63B 24/0087 482/5 |
| 2015/0141200 A1* | 5/2015 | Murray | A63B 21/154 482/5 |

* cited by examiner

| User ID |  |
|---|---|
| User | Complete Fields to the Left to Create Your Custom Profile |

| Gender |  |
|---|---|
| Female |  |

| Date of Birth | Age |
|---|---|
| January 17, 1945 | 70 |

Restart Login

| Height |
|---|
| 5 feet, 3 inches |

| Weight | BMI |
|---|---|
| 128 | 22.7 |

Done

FIG. 9

INSTRUMENTED TOTAL BODY RECUMBENT CROSS TRAINER SYSTEM

CROSS REFERENCE TO RELATED APPLICATIONS

This application is a nationalization of PCT Serial No. PCT/US2015/012837, filed Jan. 26, 2015 which claims benefit of U.S. Provisional Application Ser. No. 61/931,099, filed Jan. 24, 2014, and U.S. Provisional Application Ser. No. 61/952,529, filed Mar. 13, 2014.

BACKGROUND

1. Field of the Invention

This invention relates to an instrumented cross training device which provides for exercise, rehabilitation, and physical assessment of a user.

2. Description of Related Art

Rehabilitation and exercise devices have been created by the NuStep Inc. of Ann Arbor, Mich. NuStep pioneered a recumbent stepper machine utilizing contralateral motion between foot pedals and arm handles. The contralateral motion couples the foot pedals and arm handles such that one arm moves in the same direction as the opposite-side foot pedal and vice a versa in a repetitive motion. The device incorporates an internal energy absorber which has adjustable resistance and allows the range of motion to be adapted to the user based on the user's control. The devices including the NuStep "T4" and "T5" and other of applicant's models have enjoyed widespread adoption for residential users, rehabilitation and exercise applications, and for use in medical facilities.

SUMMARY

A physical exercise device providing a stepper like motion for a user may include a pair of foot pedals and a pair of arms for engagement by the user while seated on the seat of the physical exercise device. The pair of foot pedals and/or the pair of arms may be connected to a drive train which provides contralateral motion between the pair of arms and/or the pair of foot pedals. A pedal and arm lock mechanism may also be provided which prevents the pedals and arms from moving when in the locked state, while allowing movement of the pedals and the arms when in the unlock state.

The physical exercise device may also include a computational and data acquisition unit for receiving and recording a pedal position signal, which may be a pedal range of motion signal, and pedal force signals. A computational and data acquisition unit may be configured to receive and calculate a number of different performance variables such as performance of the user in a dynamic activity, while the drive train lock mechanism is in the unlocked state, and static activity, when the drive train lock mechanism is in a locked state. In addition, computations made by the computational and data acquisition unit may be provided to a user of the physical exercise device via a user interface screen.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

FIG. 9 illustrates a personal page wherein New Users are prompted to input information such as their gender, date of birth, height, weight, and other parameters.

DETAILED DESCRIPTION

Figure 1:
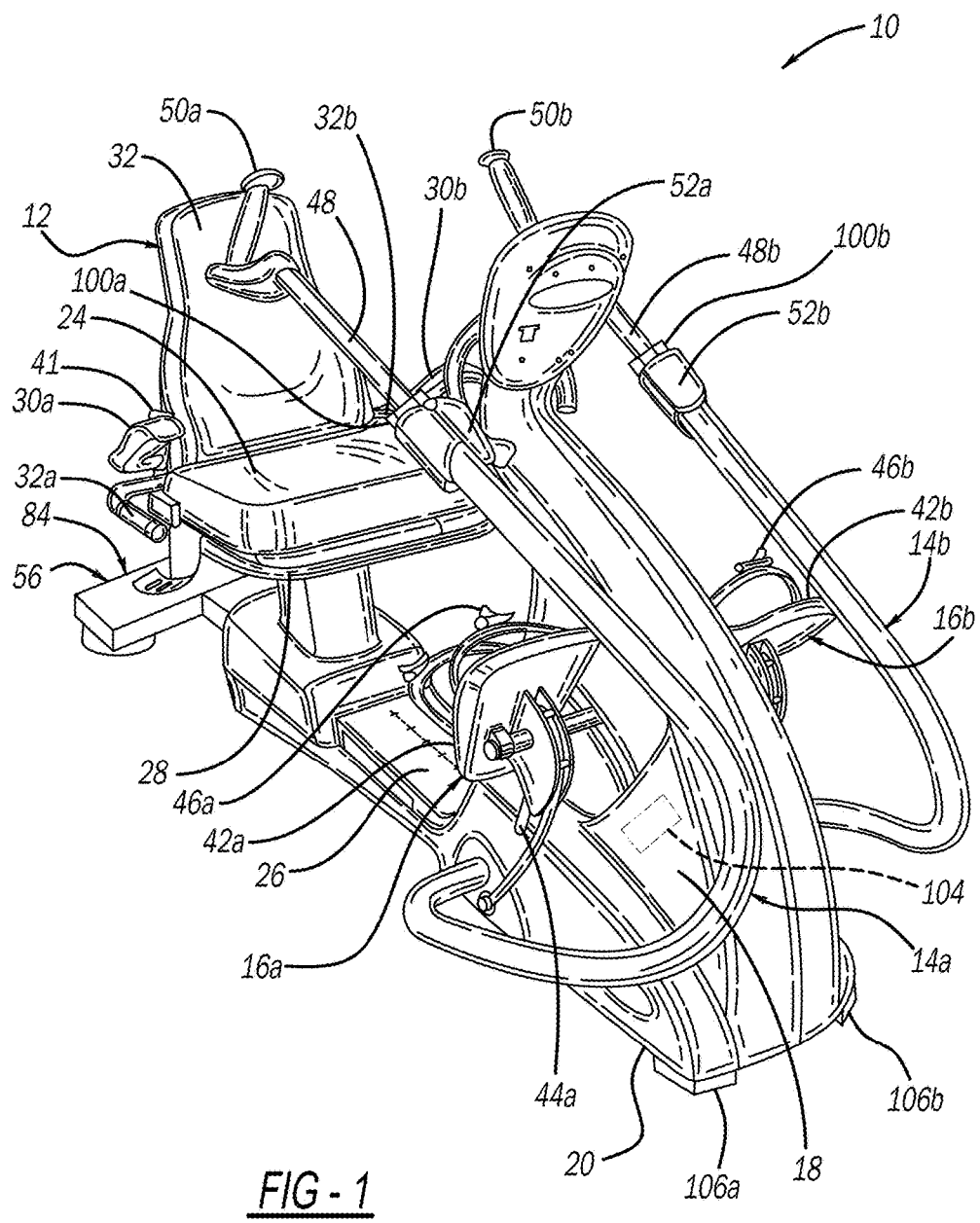
FIGS. 1-3 illustrate a physical exercise device.
Figure 2:
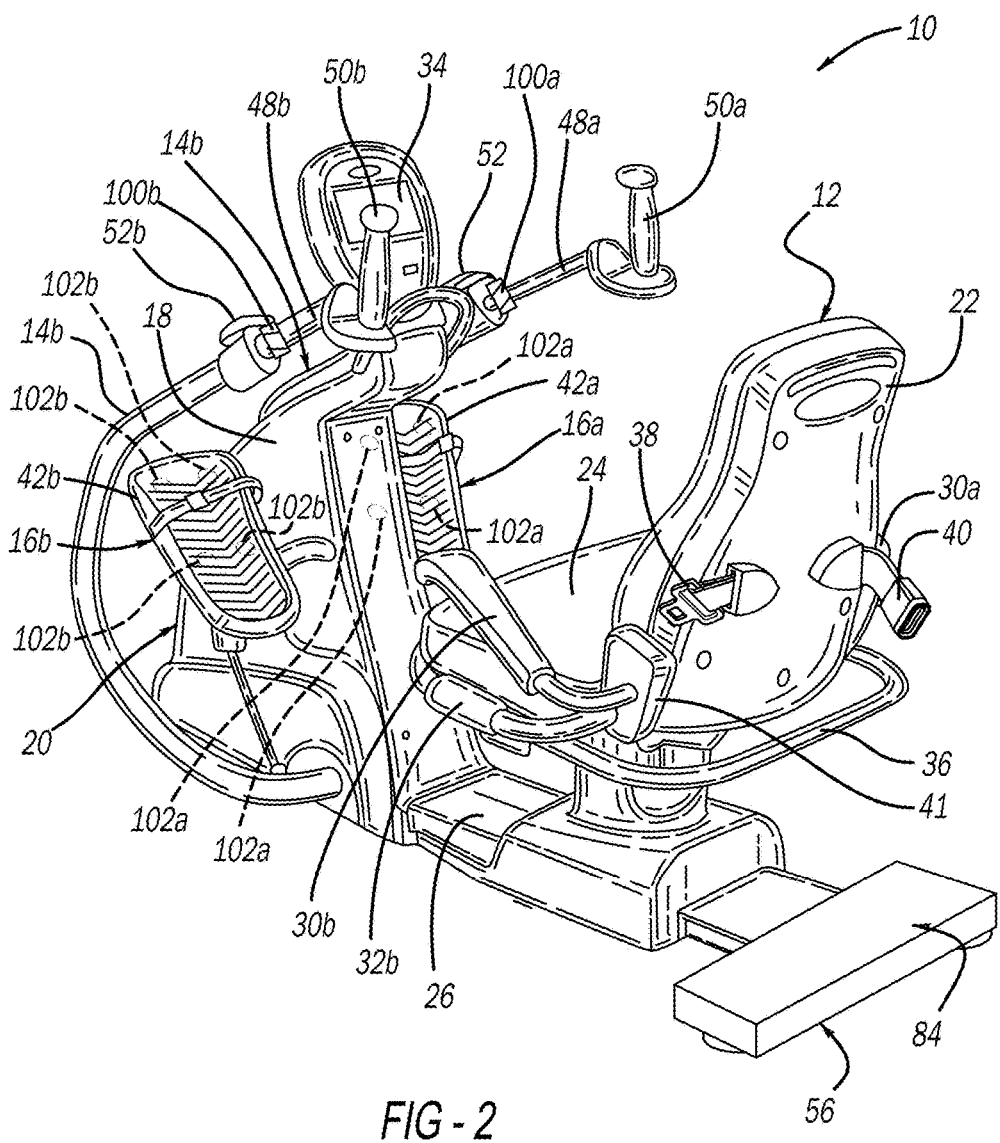
Figure 3:
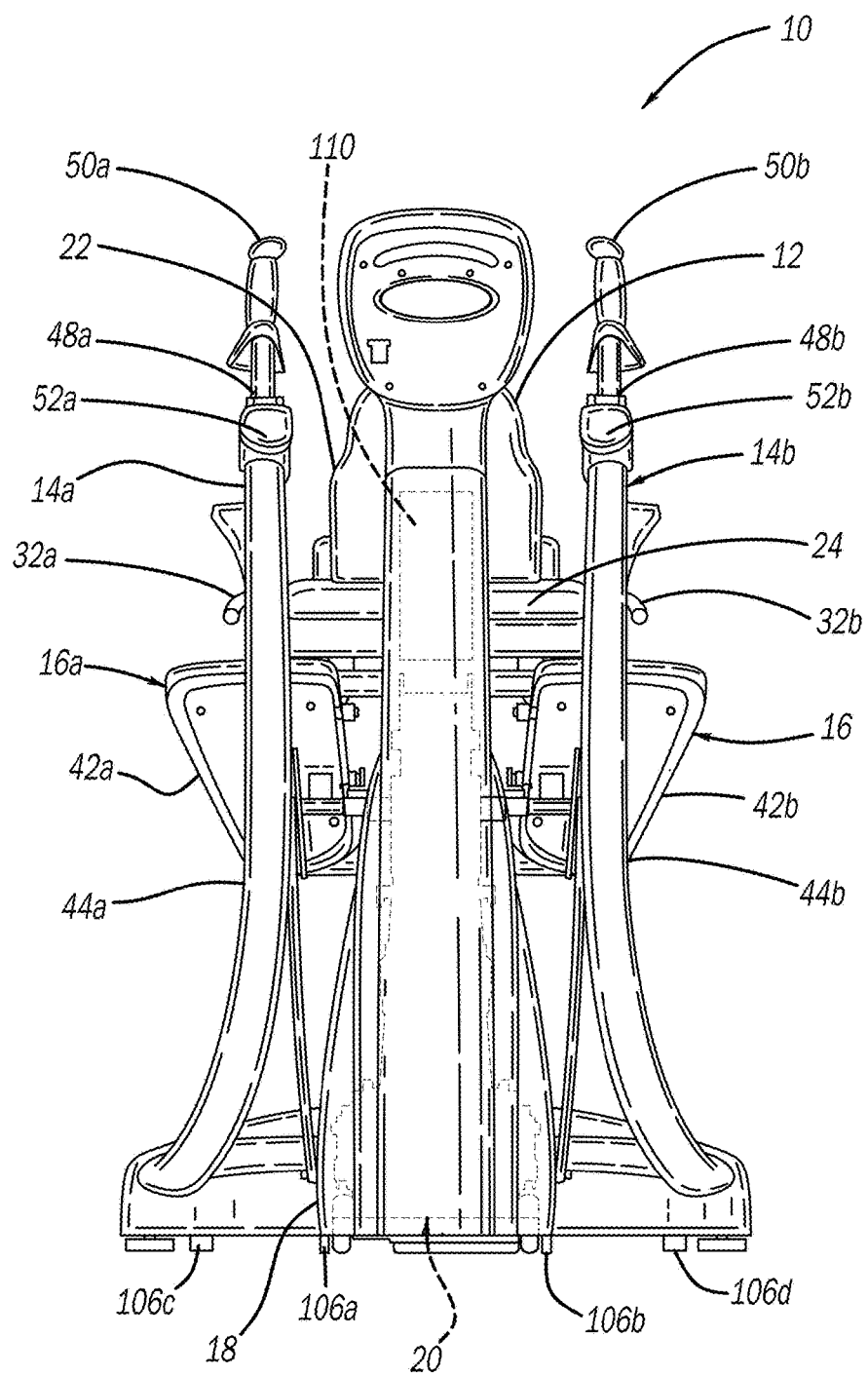
Figure 4:
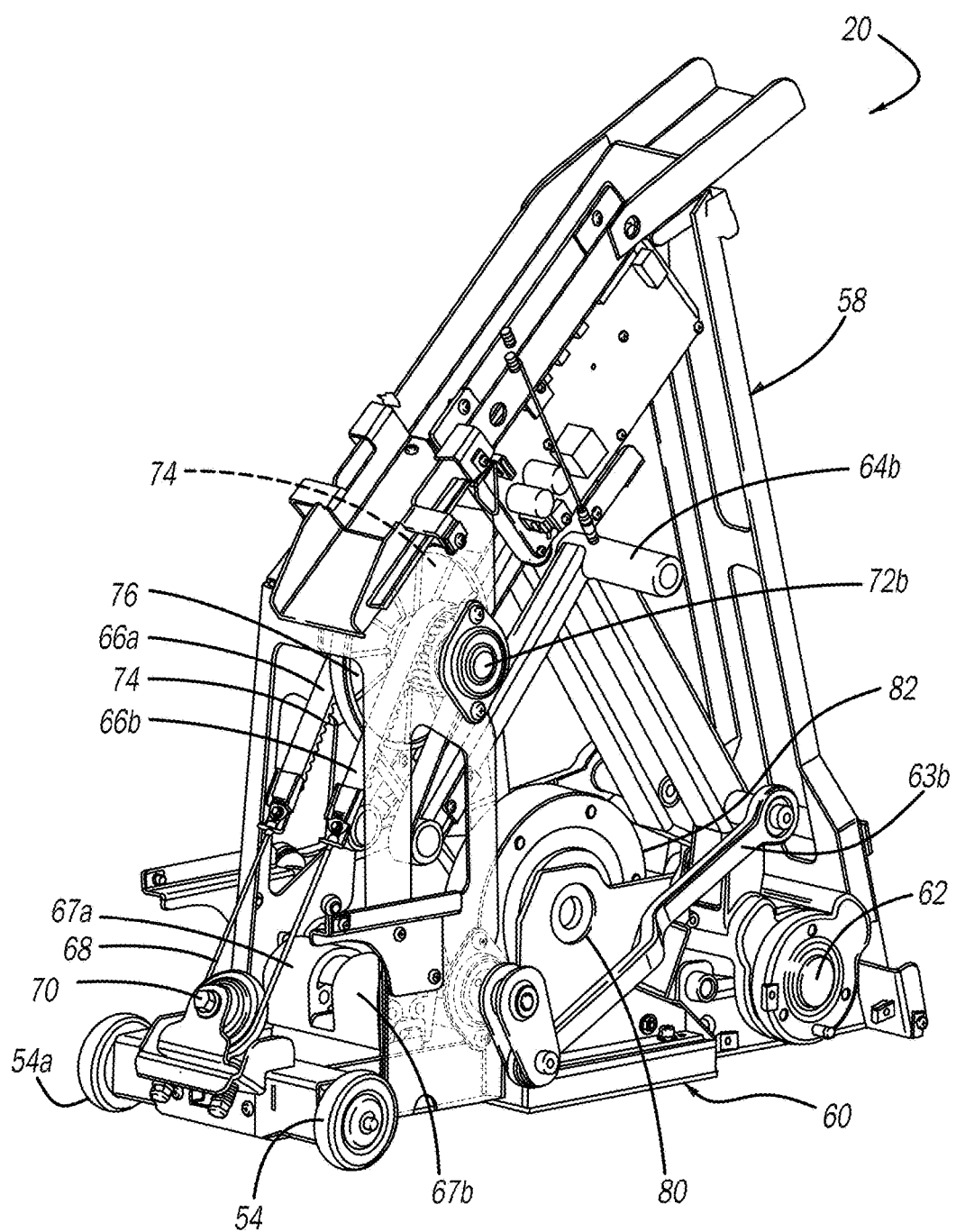
FIGS. 4 and 5 illustrate the resistance mechanism of the physical exercise device of FIG. 1-3.
Figure 5:
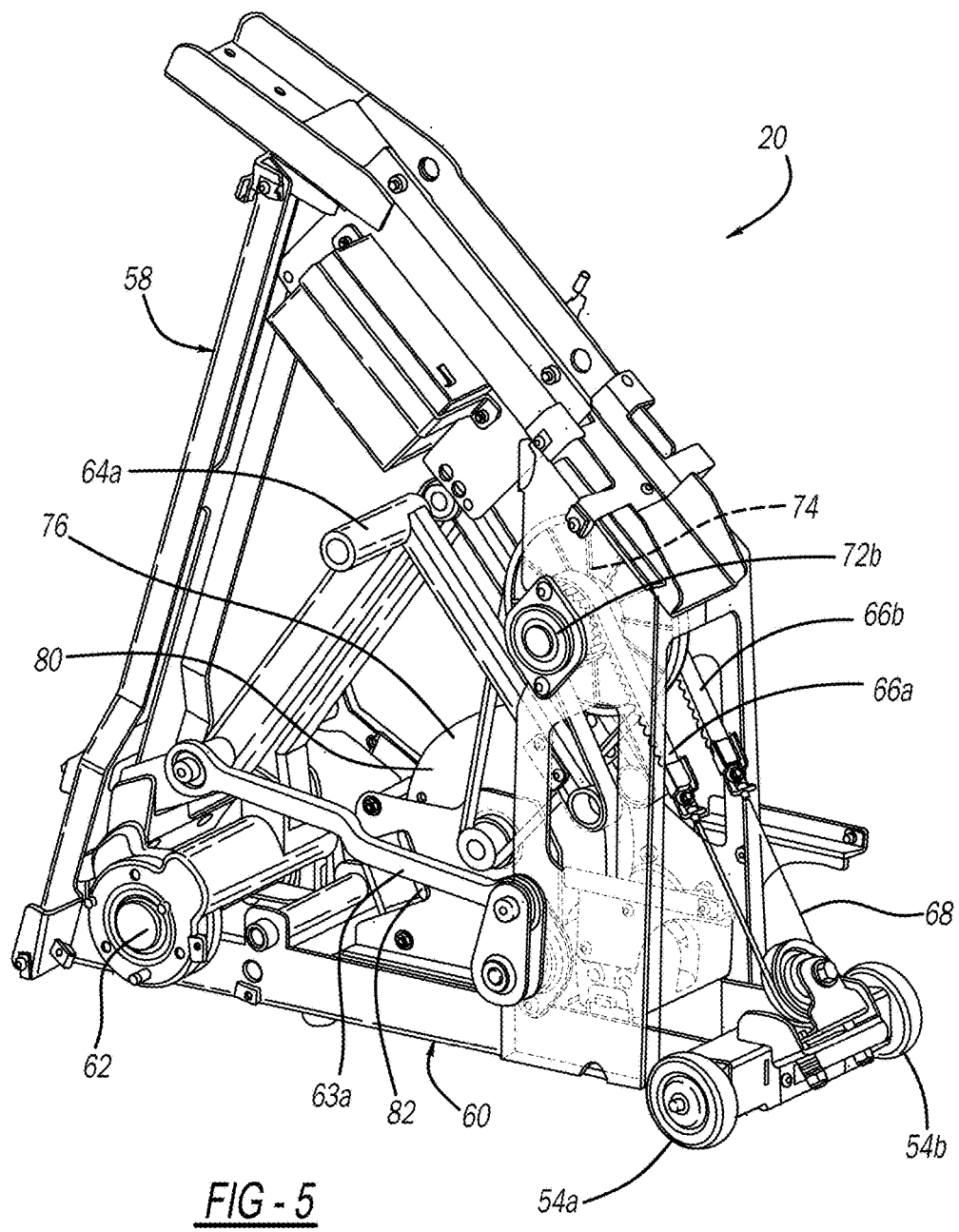

Referring to FIGS. 1, 2 and 3, a physical exercise device 10 is shown. The device 10 is a total body exerciser since it strengthens or rehabilitates major muscle groups while also providing for effective cardiovascular conditioning. The device 10 includes a seat 12, handle bar systems 14a and 14b, pedal systems 16a and 16b, and a main housing 18, enclosing a resistance mechanism 20, which is best shown in FIGS. 4 and 5. The device 10 is recumbent since the patient or user is generally in a reclined position when it is being used. The device 10 can be referred to as a cross trainer since it exercises the legs and arms of the user through an oscillating or reciprocating movement of pedal systems 16a and 16b and handle bar systems 14a and 14b through the offering of resistance to pushing or pulling (with foot straps) of the pedal systems 16a and 16b and handle bar systems 14a and 14b. Either pushing or pulling against resistance exercises the legs and lower body of the user, and the upper body and arms. It should be understood that the device 10 can take any one of a number of different forms. For example, the device 10 may be a recumbent stepper as illustrated in U.S. Pat. Nos. 6,042,518, 7,854,685, 7,785,232, or 7,775,942, all of which are hereby incorporated by reference in their entirety.

The seat 12 includes a back 22 for supporting the back of the user and a cushion 24 for supporting the bottom of the user. The back 22 is configured to recline, to accommodate a larger or heavier user. Additionally, the cushion 24 is available in a large width cushion 24, to accommodate even larger or heavier users.

The seat 12 slidably engages a track 26, which allows the seat 12 to be adjusted closer to, or farther away, from the housing 18. The position of the seat 12 can then be displayed on a display 34. In order to adjust the position of the seat, the user engages a wraparound lever 28. Another embodiment may enable wheelchair docking with the device 10. It should be noted that the track 26 has a relatively low step through height, less than about 5 inches, making it easy for a user with restricted movement to access the device 10. The seat 12 may also include a stabilizer bar for receiving accessories, such as a leg stabilization device, as shown and described in U.S. Pat. No. 7,540,830, the entirety of which is herein incorporated by reference.

The seat 12 as shown in FIGS. 1, 2 and 3 is an action position. More specifically, the seat is in the action position when the seat 12 is positioned as if the user was currently operating the device 10. However, the seat 12 also has the ability to rotate 360 degrees, away from, and back to, the action position. The user can rotate the seat 12 by engaging a wraparound lever 36. Generally, the seat 12 can rotate about an axis substantially perpendicular to the length of the track 26. Additionally, when the seat 12 is rotated from its action position, the seat 12 contains a locking mechanism for locking the seat on the track 26, preventing the seat 12 from sliding along the track 26 when the seat 12 is rotated from its action position.

Attached to the sides of the seat are arm rests 30a and 30b. The arm rests 30a and 30b are configured to rotate on an axis substantially perpendicular to the length of the device 10, so a user with restricted movement can easily access or depart from the seat 12. Near the arm rests 30a and 30b, are heart rate monitor handles 32a and 32b. Similar to the arm rests 30a and 30b, the heart rate monitor handles 32a and 32b may or may not rotate on an axis substantially perpendicular to the length of the device 10, so as to accommodate various height users. They can remain parallel with the seat cushion 24 to enable ingress/egress with the seat. As it is well known in the art, the heart rate monitor handles 32a and 32b can measure the heart rate of the user and report the results on the display 34, via either wired or wireless signals. For example, the device 10 also has the ability to accept heart rate data via a wireless connection to a heart rate sensor system chest strap.

Seat belt retractors 38 and 40 are located on the back 22 of the seat 12. The seat belt retractors 38 and 40 each contain a retractable seat belt, terminating with a male and female head, respectively. The male and female heads engage on another, locking the user in place. The seat belt retractors 38 and 40 are located relatively high, i.e. away from the user's waist and near the user's chest. By so doing, the belts strap the midsection of the user to keep them upright and making it relatively easy for the user to disengage the male and female heads. Another seat belt 41 is mounted lower to hold a user more firmly against the seat back 22 and cushion 24 similar to conventional lap belts.

An accessory bag can be attached to the back 22 of the seat 12. Generally, any type of material can be used to make the accessory bag; however, it is preferable to make the accessory bag out of a breathable material. In an effort to increase breathability and visibility of items in the accessory bag, a portion of the bag, such as the top, or even the entire accessory bag, may be made out of a mesh material.

The pedal systems 16a and 16b, each include pedals 42a and 42b, respectively. The pedals 42a and 42b are relatively large in size so as to accommodate the feet of larger users. Also, it has been discovered that some larger users generally angle their feet outward, making a regular size pedal very uncomfortable.

The feet of the user are retained to the pedals 42a and 42b by way of retaining belts 46a and, respectively. The retaining belts 46a and 46b use a ratcheting system having a release lever; however, any type of suitable retaining means may be utilized.

The pedals 42a and 42b are pivotally connected to pedal systems 16a and 16b. The pedals 42a and 42b have an axis of rotation that is substantially perpendicular to the length of the device 10. The pedals 42a and 42b may or may not pivot freely across a defined range of motion or can be locked into one, of at least two positions, by engaging handles 44a and 44b, respectively.

The handle bar systems 14a and 14b both include upper extensions 48a and 48b. Handles 50a and 50b are slidably received in the upper extensions 48a and 48b, respectively. The handles 50a and 50b can be adjusted in length or rotated and, for this reason, locking levers 52a and 52b are provided on the upper extensions 48a and 48b to secure them at the desired length. The ends of the handles 50a and 50b are generally bent upward and inward relative to the remainder of the handles 50a and 50b and are provided with padded grips for multiple hand position locations. The handles 50a and 50b may further include a plurality of locking grooves for engaging a gripping aid device, such as shown and described U.S. Pat. No. 7,490,363, the contents of which is herein incorporated by reference.

The handle bar systems 14a and 14b and, more specifically, the upper extensions 48a and 48b, may generally form a "V" shaped pattern, with the apex of the "V" away from the seat 12. By shaping the upper extensions 48a and 48b to form a "V", the distance between the handles 50a and 50b increases as the handles 50a and 50b are extended in length, so as to more readily accommodate larger users. So, the width between the handles 50a and 50b adjusts narrower or wider based on the distance the upper extensions 48a and 48b are extended.

Referring to FIGS. 1 and 4, the device 10 includes wheels 54a and 54b (shown in FIG. 4), located under the housing 18, opposite of the seat 12. With the device 10 situated on a flat surface, the wheels 54a and 54b are two points out of four contacts with the flat surface. However, a specialized dolly can engage a back portion 56 of the device 10, lifting the back portion 56 off the flat surface. As the back portion of the device 10 is listed off the flat surface, the wheels 56a and 56b rotate thereby making the device 10 highly portable.

Referring to FIGS. 4 and 5, a more detailed view of the resistance mechanism system 20, which, as previously stated, is enclosed by housing 18. The mechanism 20 is supported in part by a frame 58 and a base 60. A central pivot 62 provides the pivot axis wherein the handle bar systems 14a and 14b, and pedal systems 16a and 16b rotate from. The handle bar systems 14a is rigidly coupled to the pedal system 16b and the handle bar system 14b is rigidly coupled to pedal the system 16a for contralateral motion about the central pivot 62. This rigid coupling will cause the handle bar system 14a and the pedal system 16b (forming a first assembly) and the handle bar system 14b and the pedal system 16a (forming a second assembly) to move together. It should be noted that the pedal systems 16a and 16b are further supported by stabilizer bars 63a and 63b, respectively. By so doing, portions of the load can be removed from the central pivot 62, extending the operating life of the mechanism 20.

The handle bar system 14a and the pedal system 16b drive an arm 64a, while the handle bar system 14b and the pedal system 16a drive an arm 64b. The arms 64a and 64b, rotate about the central pivot 62, and engage belts 66a and 66b, respectively. The belts 66a and 66b are connected to each other via a cable 68, which engaged a pulley 70. The belts 66a and 66b engage one way clutches 72a and 72b, respectively. Bumpers 67a and 67b may be positioned on the base 60, so as to absorb the motion of the pedals 16a and 16b and arms 64a and 64b, respectively. By so doing, the bumpers 67a and 67b provide a soft, low impact, fluid return motion.

The one way clutches 72a and 72b are connected to and drive a main pulley 74. The main pulley 74 then drives a main pulley belt 76, which transfers the load to the brake assembly 80, which provides the resistance. The resistance provided by the brake assembly 80 can be adjusted so as to provide more or less resistance to the user.

Essentially, the mechanism 20 only requires two stages to transfer a load provided by the user to the brake assembly 80. The first stage transfers load to the main pulley 74 from the arms 64a and 64b via the belts 66a and 66b, which engage one way pulleys 72a and 72b, respectively. The second stage transfers load from the main pulley 74 to the brake assembly 80 via the main pulley belt 76, which is connected to the brake assembly 80. Additionally, the entire mechanism 20 is compact, so as to fit between the legs of the user, but durable enough to withstand significant loads for long periods of time.

Referring back to FIGS. 1 and 2, the device 10 may also have a step platform 84 located rearward of the seat 22. The step platform 84 may be engaged by the user when the user places one or more feet on the step platform 84. The engagement of the step platform 84 can be aided by the seat 12, wherein the user grasps at least a portion of the seat 12 so as to aid with stepping on the a step platform 84 of the device 10.

As stated previously, this is but one embodiment of the claimed invention. The device 10 may be any one of a number of different exercise devices and the claims should not be just limited to this specific claimed embodiment of the recumbent stepper device 10 of FIGS. 1-5.

The device 10 may also include any one of a number of different sensing devices, data acquisition units, and a computation device or devices for determining the performance of the user as the user uses the device 10. For example, referring to FIGS. 1, 2, and 3, the arm assemblies 14a and 14b may each be outfitted with arm force sensors 100a and 100b, respectively. The arm force sensors 100a and 100b are configured for measuring force applied to each arm by the user. Further, referring to FIG. 2, pedal assembly 16a and 16b may have one or more force plates for measuring forces exerted by the user on each of the pedals 42a and 42b. Furthermore, referring back to FIG. 1, a position sensor 104 may be located within the housing 20 and be configured to determine the positions within the range of motion of each of the arm assemblies 14a and 14b and/or the pedal assemblies 16a and 16b.

The device 10 may also include sensors for measuring the weight of the device 10 on the ground. For example, referring to FIGS. 1 and 3, the front of the device 10 may include forward weight sensors 106a and 106b, while the rear device 10 may include rearward weight sensors 106c and 106d. The weight sensors 106a-106d can measure the weight of the device at different corners of the device 10.

Figure 6:
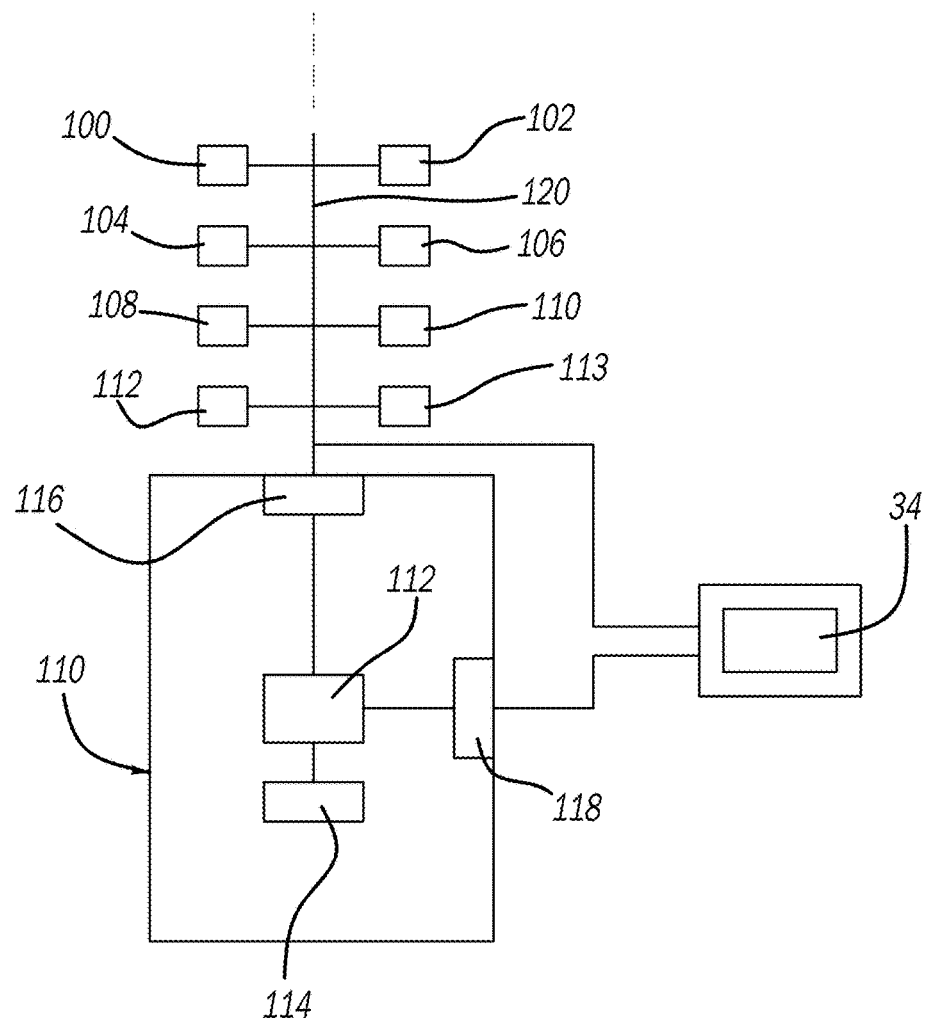
FIG. 6 illustrates a block diagram of a computational device of the physical exercise device of FIG. 1-3.

Referring to FIGS. 3 and 6, the device 10 may also include a computational and data acquisition unit 110 which may be located within the housing 18. Of course, it should be understood that the computational device may be located in places other than the housing 18 and may take any one of a number of different forms. As an example, referring more specifically to FIG. 6, the computational and data acquisition unit 110 may include a processor 112 which is an electrical communication with a memory 114. The memory 114 may contain instructions configuring the processor 112 to perform any one of a number of different methods or applications disclosed in this specification. It should be understood that the memory 114 may be located separate from the processor 112 or may be integrated within the processor 112. Of course, it should be understood that the computational and data acquisition unit 110 may be a distributed unit with different functionalities located in different distributed areas. For example, the computation part and the data acquisition part may be separate and located remote from each other.

The processor 112 may also be in electrical communication with an input port 116 and an output port 118. The input port 118 can provide any one of a number of different inputs to the processor 112. It should be understood that the input port 116 can be any one of a number of different methodologies for providing input to a processor 112. For example, the input port 116 could be any one of a number of known standards such as serial, parallel standards or even specific industry standards such as Ethernet, USB, FireWire, and the like. Additionally, the input port 116 may also utilize a wireless protocol, such as Wi-Fi or Bluetooth. The output port 118, like the input port 116, may utilize any one of a number of different methodologies listed above regarding the output port 116. In like manner, the output port 118 could also be a wireless communication, such as Wi-Fi or Bluetooth. Further, it should be understood that the input port 116 and the output port 118 may in fact be the same port or utilize a common chipset for providing inputs and/or outputs to the processor 112.

The sensors described in the previous paragraphs may be connected either directly or via a bus 120 to the input port 116. As stated before, these sensors may include arm force sensors 100, pedal force plate sensors 102, position sensors 104, weight sensors 106, or other sensors 108. Additionally, other sensors may be utilized with the device, including a seat position sensor 111 for determining the position of the seat 12 along the track 26 or other sensors 113 to measure any one of a number of varieties of variables of the device 10 or even the user, such as biometrics of the user, including pulse rate of the user or sensors 113 for identifying the extension length of the arms as the handle telescopes toward and away from the primary arm tubes of assemblies 14a and 14b.

Any one of a number of different methodologies may be employed for transmitting signal data to the processor 112. For example, the signals from these sensors may be passed through signal conditioning electronics and converted from analog signals to digital data which are then ported to the processor 112. The position data can come in a variety of forms but is ultimately captured in a digital format and ported to the processor 112 as well. The arm extension length may be handled in a fashion similar to the seat position or other methodology.

As stated before, the device 10 also includes a display device having a display area 34. The display area receives inputs from the processor 112 by the output device 118. The display device 34 may also act as a touch screen input device with either touch screen functionality or buttons. In either case, the display device 34 may also be connected to the input device 116, so as to receive any inputs from the user while using the display device 34.

Further, it should be understood that the display device 34 may be an external display device. This external display device may be a mobile phone or tablet computer capable of displaying information for and or from a user of the device 10 and receiving inputs from the user of the device 10. Essentially, this mobile phone or tablet computer may entirely replace the display device 34.

The computational and data acquisition unit 110 can receive the position signal of the pedals/arms from the position sensor 104, the pedal force sensors 102, and/or arm force sensors 100 and record the pedal force signals and/or arm force signals over the range of motion of the drive train for enabling computation of performance of the user in a dynamic activity while the drive train lock mechanism is an unlocked state and static activity with the drive train lock mechanism in the locked state.

The computational device 110 may also be configured to measure the power expenditure by the user while in the dynamic activity, identify a power output and energy exerted by the user through each of the pedal or arms in the dynamic activity, and identify force exerted by the user at the pedals or arms in the static activity or the dynamic activity. These calculations may be provided to the user via the display 34 through a user interface utilizing biofeedback graphics for the user and enabling data input by the user. A power computation may be calculated by using data received from the position sensor 104 and the pedal and arm force sensors 102.

The computational device 110 may also be capable of executing any one of a number of different activities or applications which will be described in the paragraphs and figures that follow. For example, the computational device may be configured to carry out a pace partner, a progressive load test and heart rate recovery test, a muscle endurance test, a balance, power and work output application, an exercise intensity histogram, a climbing application, a maximum force test, a force limiting graphical warning, a berg balance test, a balance abc score, a physical performance test, a force versus time isometric training, and a subMax fitness test. In like manner, the computational device 110 may be configured to determine a pain assessment score, a perceive exertion scale, an angina scale, a claudication scale, and a dyspnea scale.

The computational and data acquisition unit may also be configured for enabling games to be played. These games can include a force control target hunting game, a force controlled path tracking game, an isometric pong, and a range of motion pong. The computational and data acquisition unit may provide information to the user via the display 34 using a metronome, a power graphic for each pedal or arm, and a center of pressure graph for pedal forces and/or user body weight.

Figure 7:
FIG. 7 illustrates an opening screen for the graphical user interface.
Figure 62:
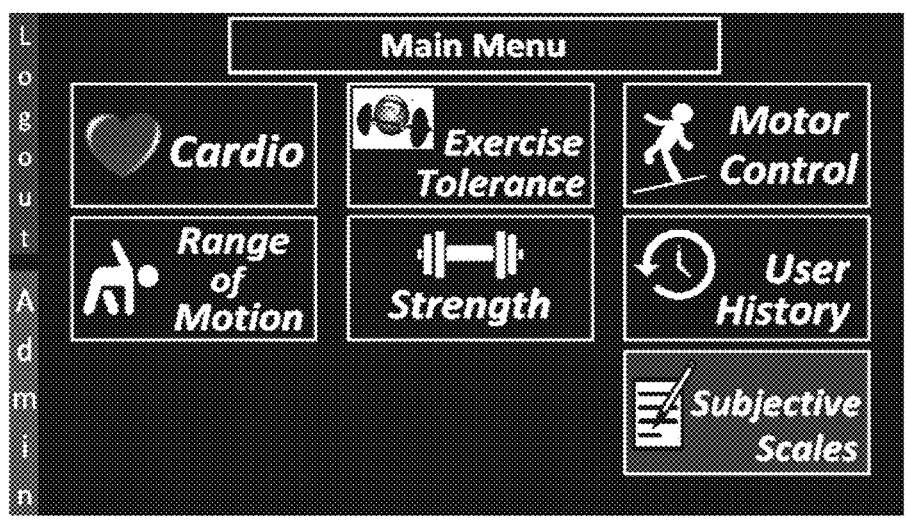
FIG. 62 illustrates a main menu user interface.

FIGS. 7-62 each show a screenshot that may be provided to the display 34 from the computational and data acquisition unit 110. As stated before, the display device 34 may be a dedicated device attached to the device 10, or may be a separate device, such as a mobile phone or tablet computer.

These screenshots illustrate any one of a number of different games and information that may be provided to the user of the device 10. It should be understood that these screenshots are examples of the games and information that may be provided to the user of the device 10. Inputs for playing the games or determining information may be provided by the user when the user steps on the stepper device 84 or utilizes the pedal systems 16a and 16b and/or handle bar systems 14a and 14b. Further information be can provided by the sensors of the device 10. As stated before, these sensors may include arm force sensors 100, pedal force plate sensors 102, position sensors 104, weight sensors 106, or other sensors 108. Additionally, other sensors may be utilized with the device, including a seat position sensor 111 for determining the position of the seat 12 along the track 26 or other sensors 113 to measure any one of a number of varieties of variables of the device 10 or even the user, such as biometrics of the user, including pulse rate of the user. Additionally, the sensors 113 may measure the extension length of the arms as the handle telescopes toward and away from the primary arm tubes. Such sensors 113 can aid in return user setup as well as assist in improving calculations of torque applied to the arms which in turn improves measures of power applied by the user's arms.

Further, the computational and data acquisition unit 110 may be configured to generate reports, set goals, see progress toward the goals, generate protocols which string one or more applications described in this specification together to form defined sequences for universal and custom use by users. The computational and data acquisition unit 110 may track user biometrics and performance, such as changes in weight over time.

Figure 8:
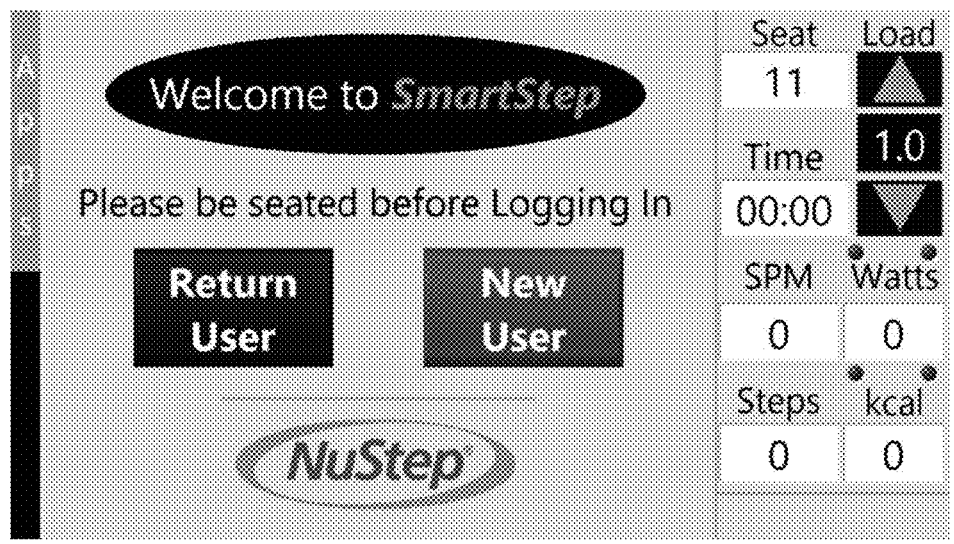
FIG. 8 illustrates a welcome screen wherein the user indicates whether he or she is a Return User or a New User.

FIG. 7 shows an opening screen for the graphical user interface (GUI) to be shown on the display 34. The screen image such as that shown in FIG. 8 illustrates a welcome screen wherein the user indicates whether he or she is a Return User or a New User. The user then proceeds to enter a user ID and password to create and/or access a user-specific database. FIG. 9 illustrates a possible personal page wherein New Users are prompted to input information such as their gender, date of birth, height, weight, and other parameters. Age is automatically calculated and updated. For systems with weight measurement capability, the weight may be acquired from system sensors. This page can be accessed by Return Users through other means if they wish to update any of the parameters. User weight assists with customizing default load levels/settings on a number of the tests and games. Subsequent measures of weight will be tracked to document changes in weight over time. With these inputs the system can calculate a body mass index (BMI) value for the user.

Figure 10:
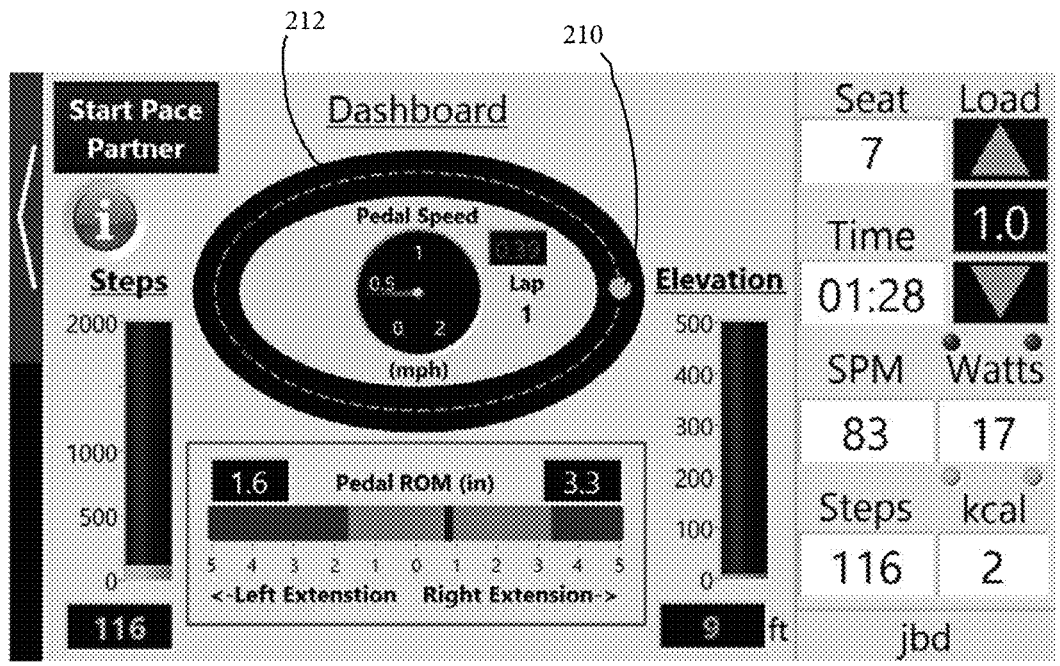
FIGS. 10 and 11 illustrate a "pace partner" game.
Figure 11:
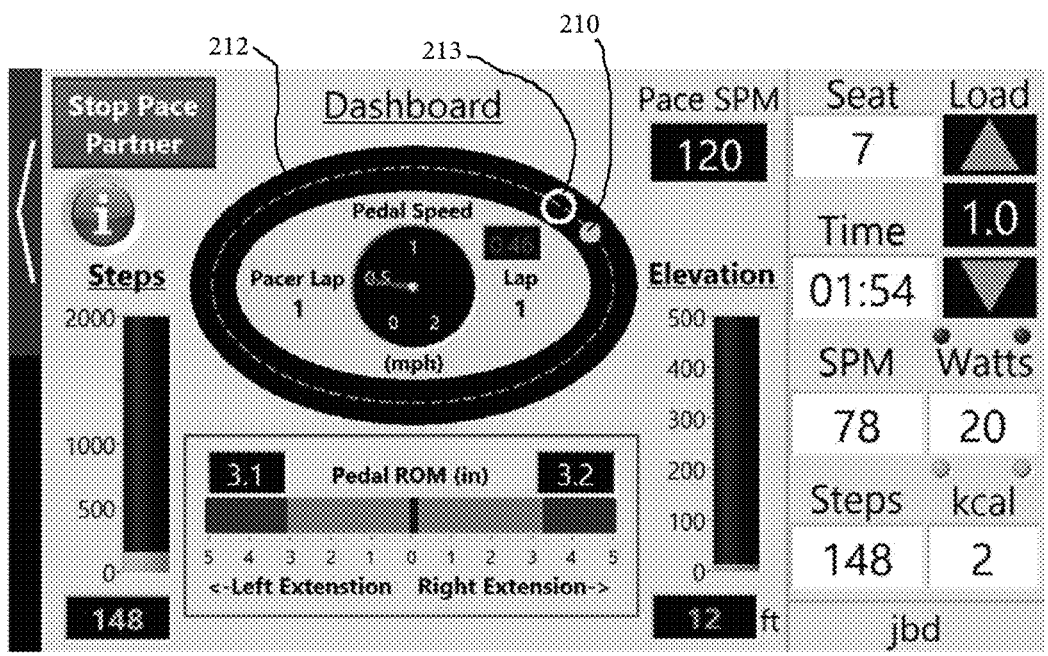

FIGS. 10 and 11 further illustrate the use of a functionality referred to as a "pace partner". This is a game played by the user in which a virtual runner 210 (bicycle rider, swimmer etc.) moves around a virtual oval track 212. By exerting forces on the device 10, the user causes an icon 213 to move along the elliptical closed course 212. Visual cues are provided to indicate if the user is behind, at, or ahead of the selected pace. For example, the color of the user's icon can change when it is within, behind, or ahead of the circle indicating progress of the pace partner.

Figure 12:
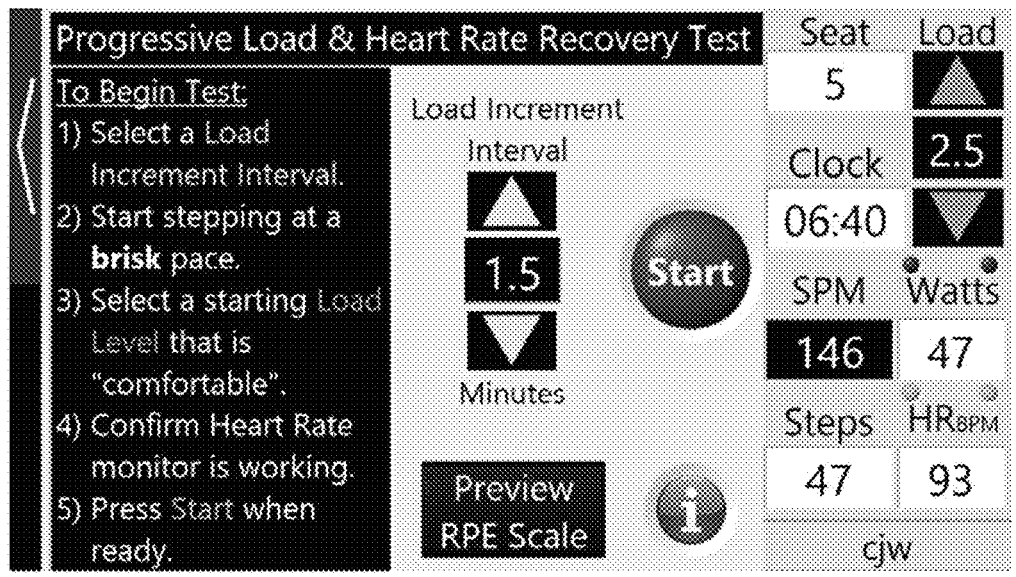
FIG. 12 illustrates a GUI for beginning the progressive load and heart rate recovery test.
Figure 13:
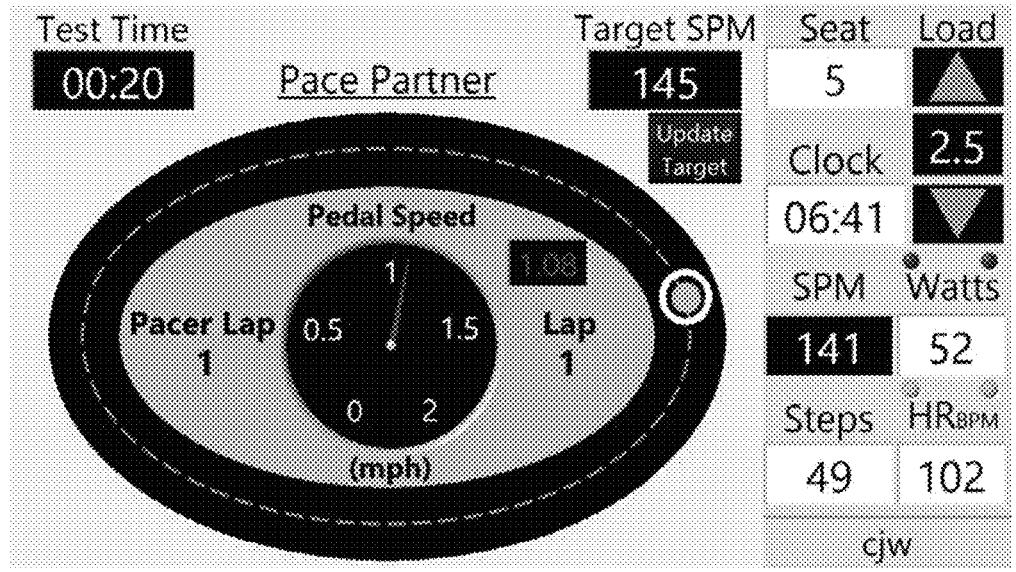
FIGS. 13-17 illustrate user interfaces for a sequence of events that occur during the progressive load and heart rate recovery test.
Figure 14:
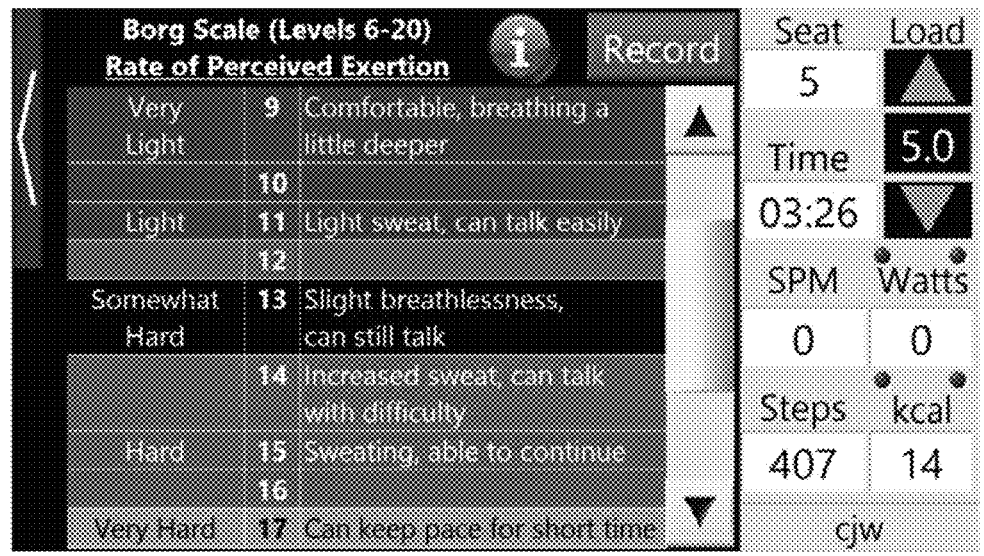
Figure 15:
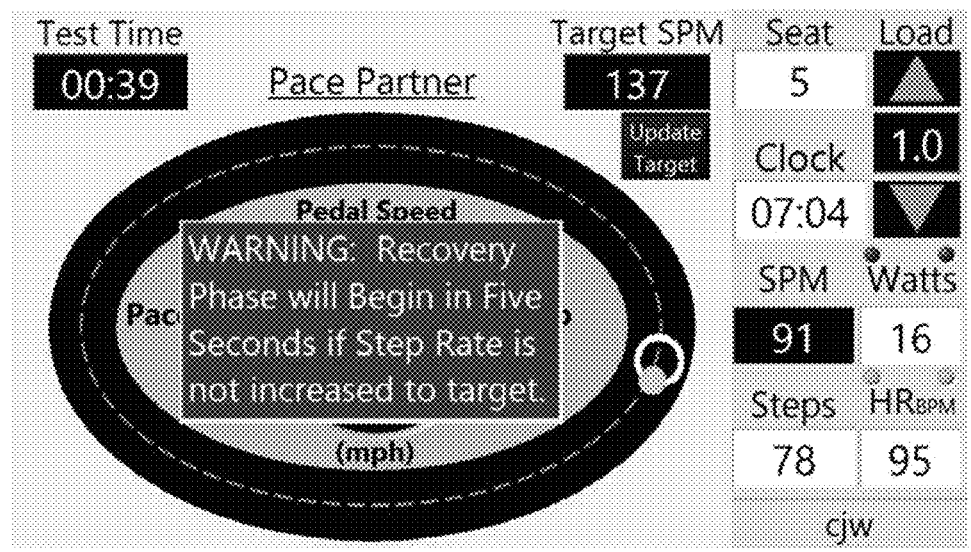
Figure 16:
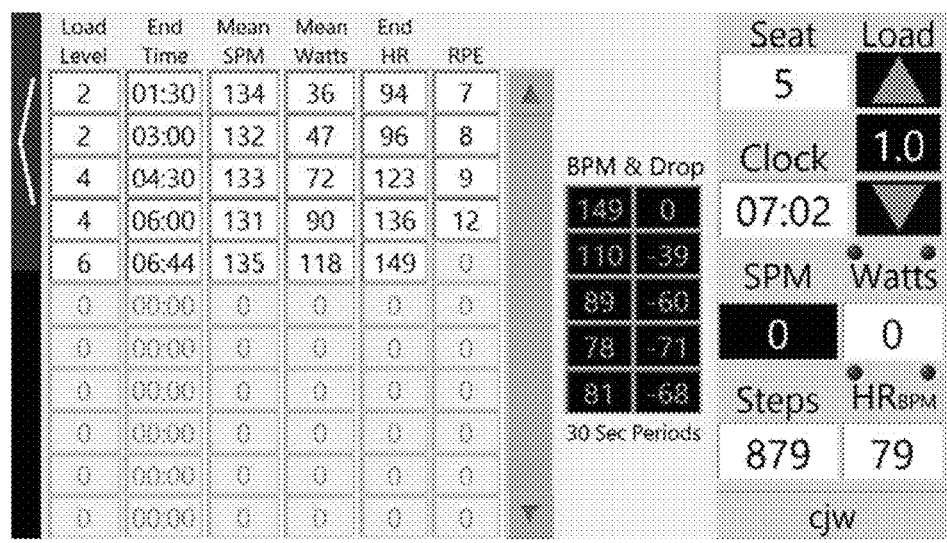

FIG. 12 shows a screenshot of the initial GUI for setting parameters for and beginning the progressive load and heart rate recovery test.

Figure 17:
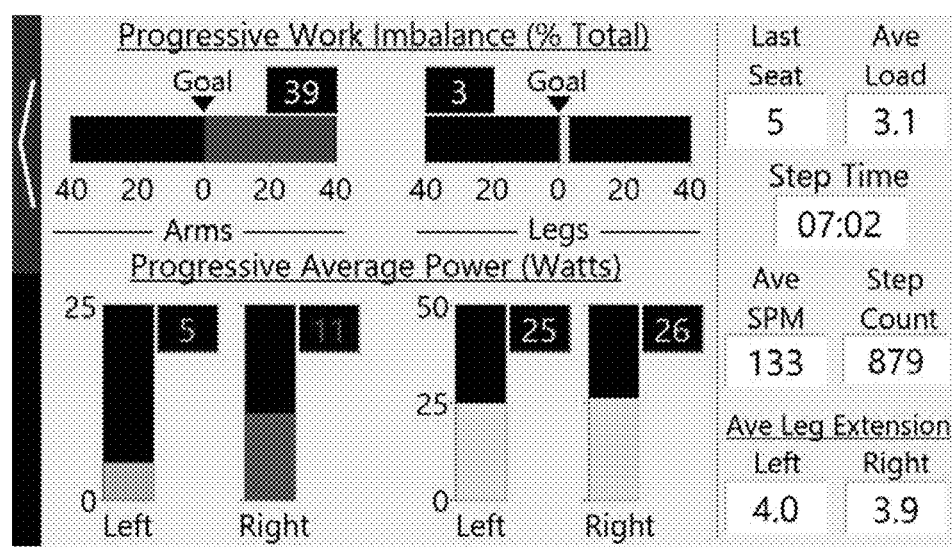

FIGS. 13-17 illustrate screenshots of a sequence of events that occur during the progressive load and heart rate recovery test following the beginning screen (FIG. 12) which includes a pace partner to facilitate the user's ability to maintain a constant step rate (FIG. 13), a rate of perceived exertion that pops up during each interval for the user to report their respective effort for each load level stage (FIG. 14), a warning indicating to the user to pick up his or her pace to the desired step rate or the stepping phase of the test will end (FIG. 15), an image of the results of the heart rate recovery phase (FIG. 16), and an exercise balance display that is provided after the test to show left right balance of arms and legs during the stepping phase of the test (FIG. 17). The exercise phase may also be programmed to stop automatically if the user stops stepping for a preset period of time.

Figure 18:
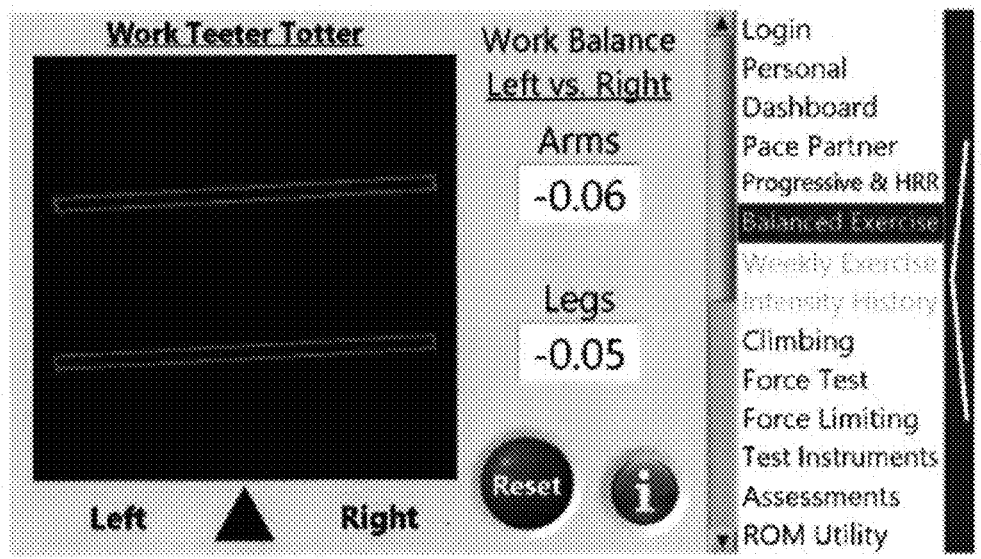
FIGS. 18 and 19 illustrate a "work teeter totter" work balance test.
Figure 19:
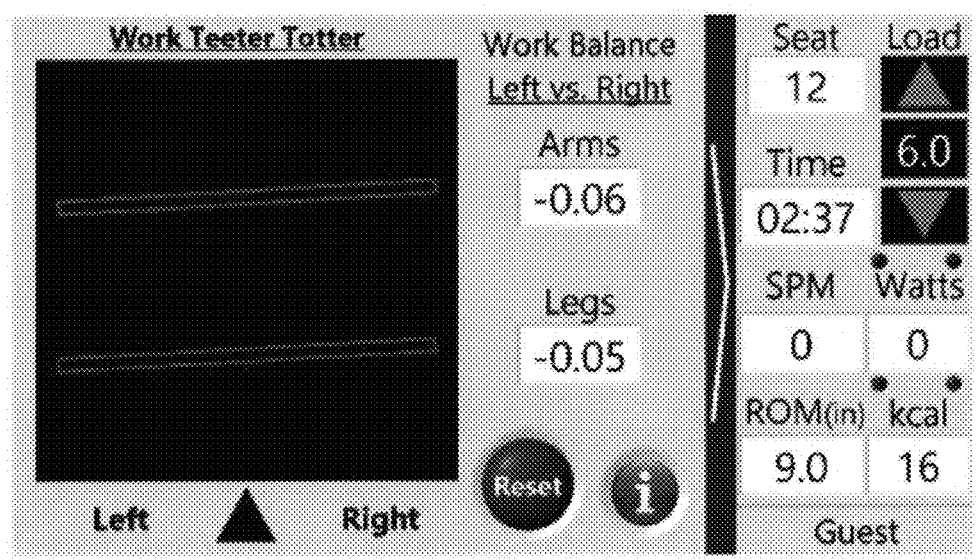
Figure 20:
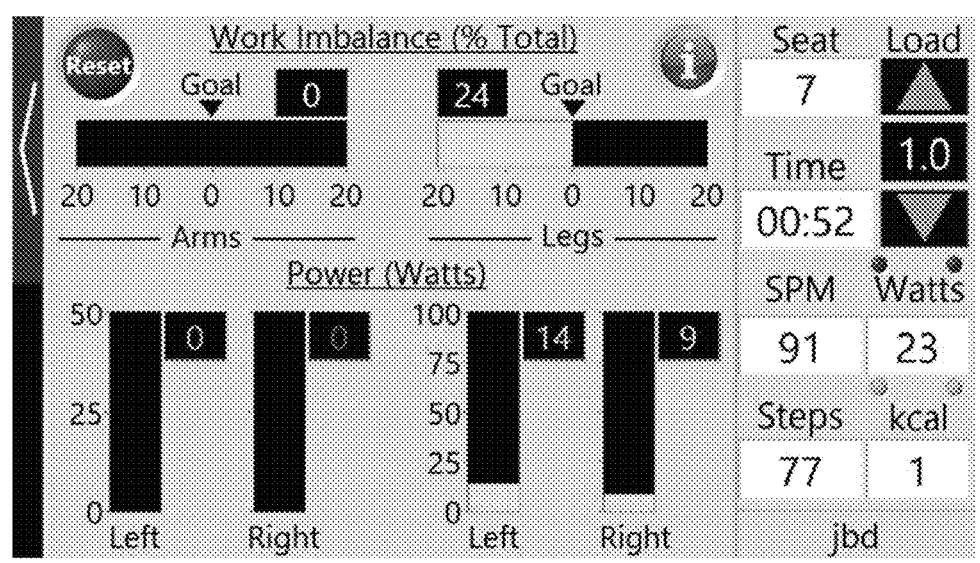
FIG. 20 illustrates a user interface for power and work imbalance monitoring.

FIGS. 18 and 19 are screenshots related to a "work teeter totter" work balance test which provides a graphical output 214 related to balance and imbalance in forces exerted by left and right legs and/or arms of the user. This tool can be used to enable equalization of power exerted by left and right arms and legs on the handle bar systems 14a and 14b and/or pedal systems 16a and 16b. Further, FIG. 20 illustrates a user interface of a representation of the ability of the unit to display real time power output of each limb and work balance between left and right arms and legs.

Figure 21:
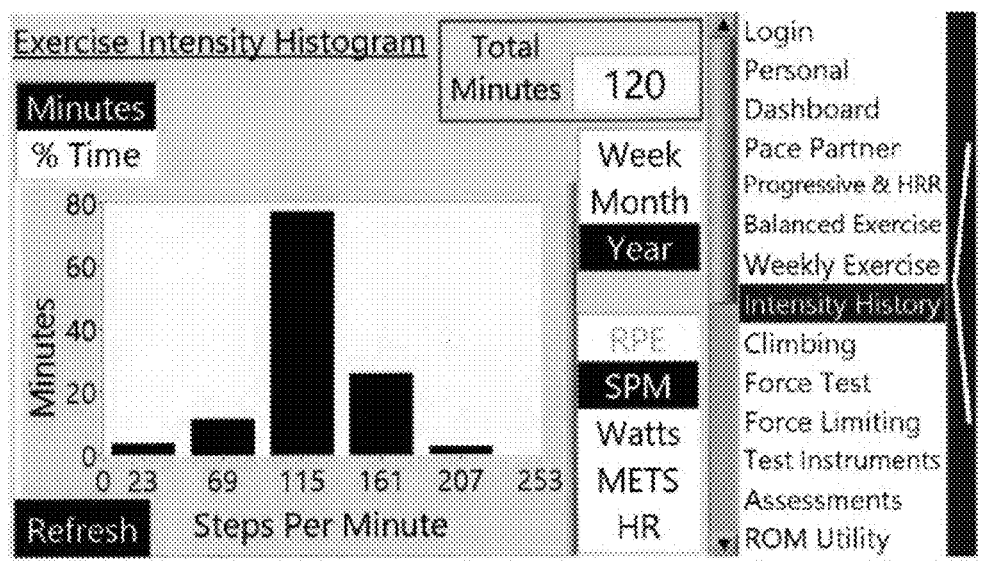
FIGS. 21 and 22 illustrate exercise histograms for example exercise histories.
Figure 22:
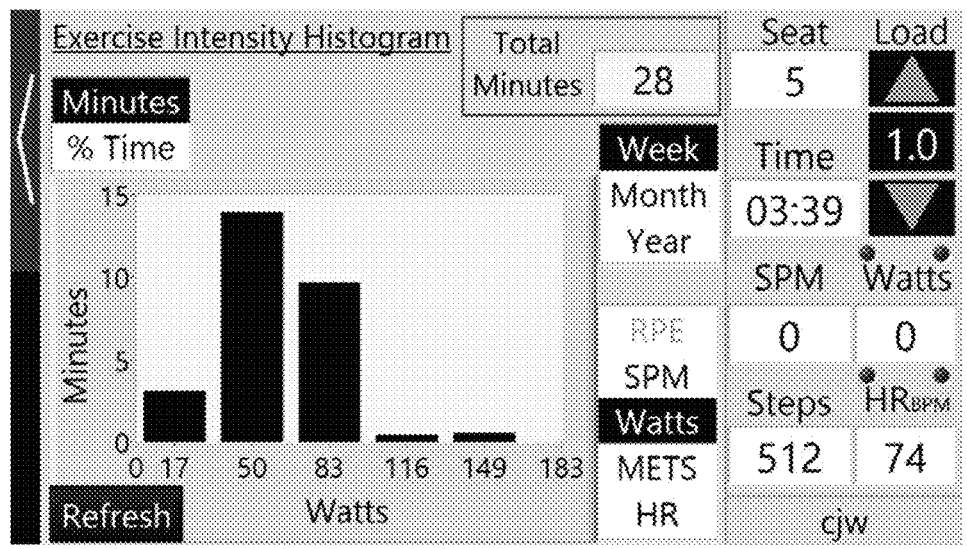

FIGS. 21 and 22 provide exercise histograms for example exercise parameters, SPM and Watts, over selected periods of time, a year and a week, respectively.

Figure 23:
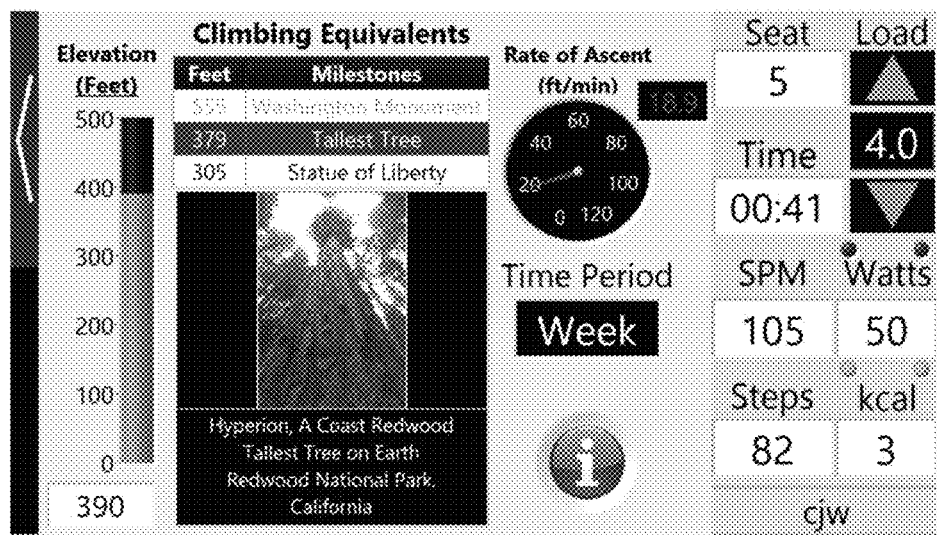
FIGS. 23 and 24 illustrate user interfaces for a climbing equivalent game
Figure 24:
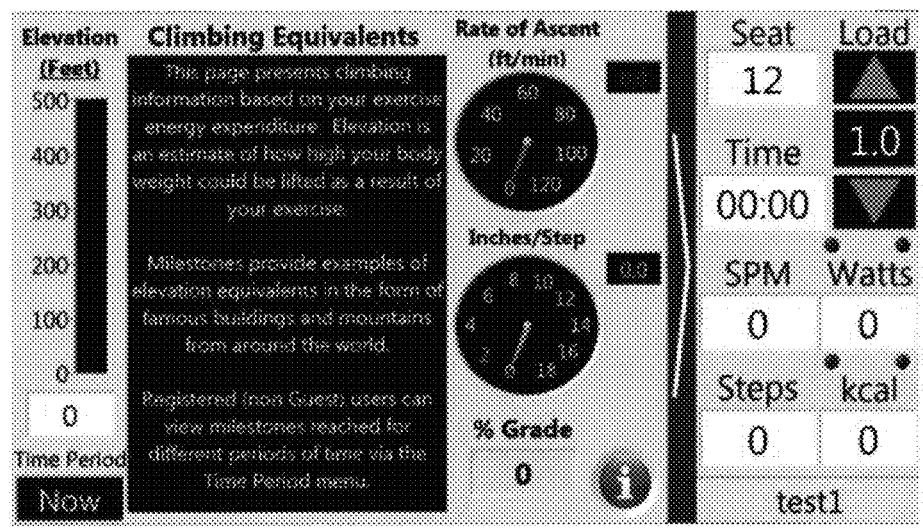

FIGS. 23 and 24 illustrate user interfaces for a climbing equivalent game in which energy expended by the user as he or she performs activity on the device is used to simulate elevation changes for various virtual real objects such as buildings or landscape features, or notional structures.

Figure 25:
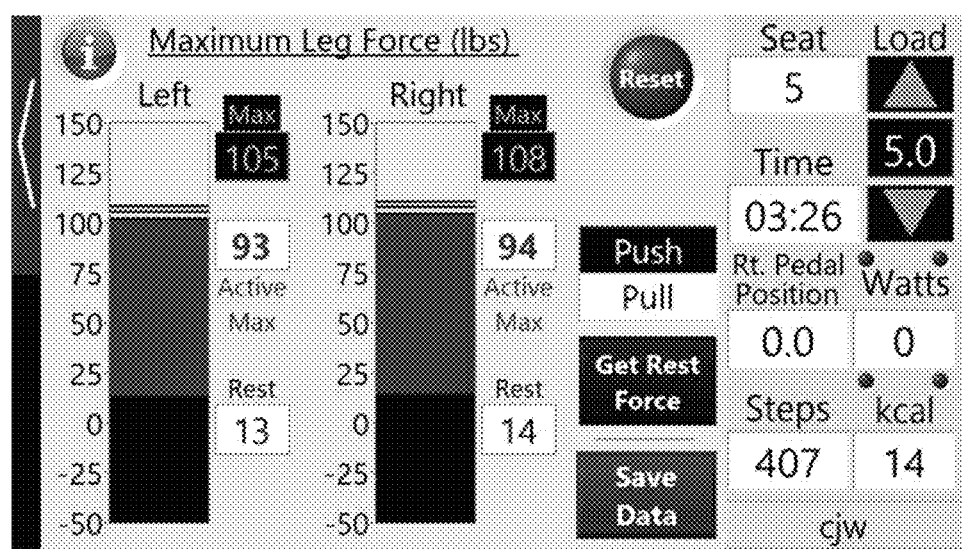
FIG. 25 illustrates an interface related to a maximum force test.

FIG. 25 provides an example illustration related to a maximum force test. The test involves locking of the arms and legs of the device and measuring a maximum isometric force exerted by the user on the handle bar systems 14a and 14b and/or pedal systems 16a and 16b.

Figure 26:
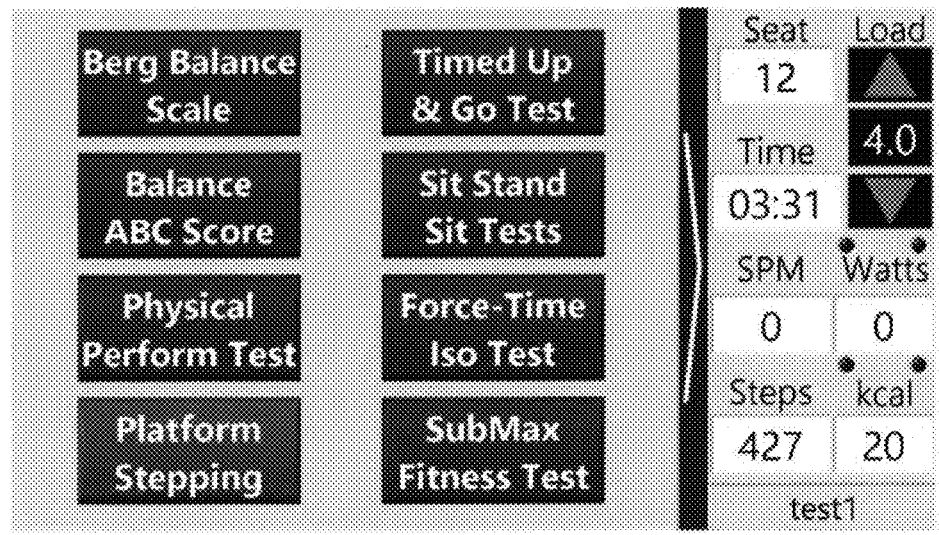
FIG. 26 illustrates a variety of various standardized tests which may be performed using the device.
Figure 27:
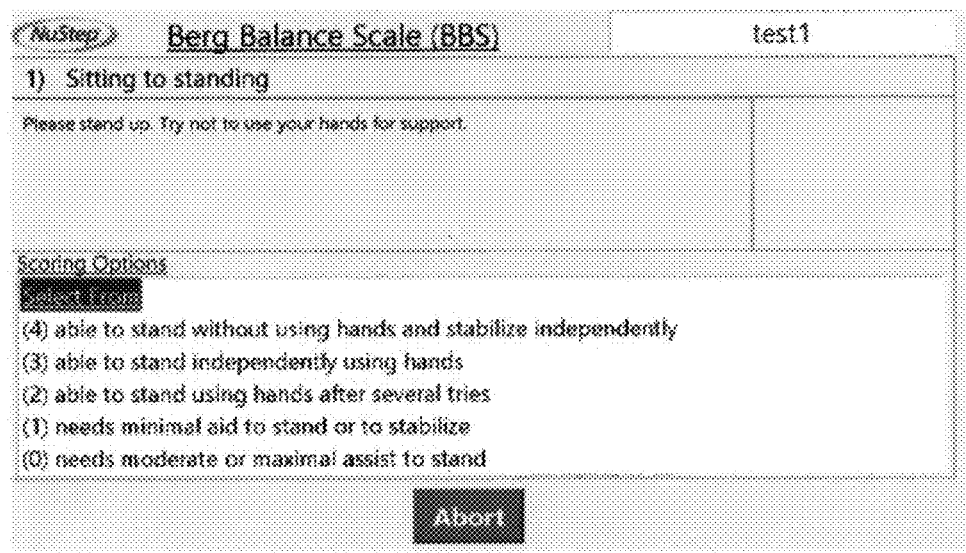
FIG. 27 illustrates a Berg Balance Scale test.
Figure 28:
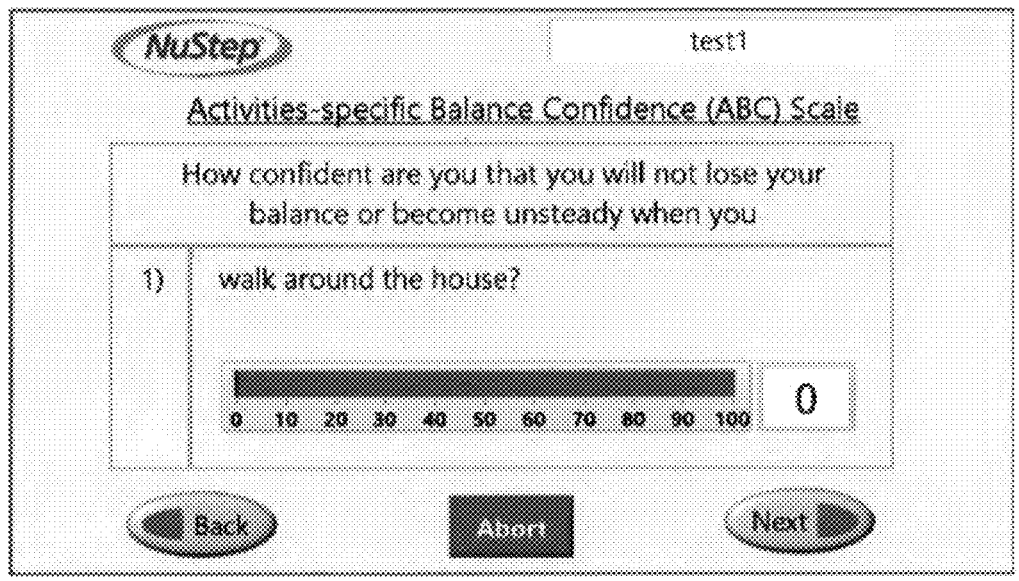
FIGS. 28 and 29 illustrate an Activities-specific Balance Confidence test.
Figure 29:
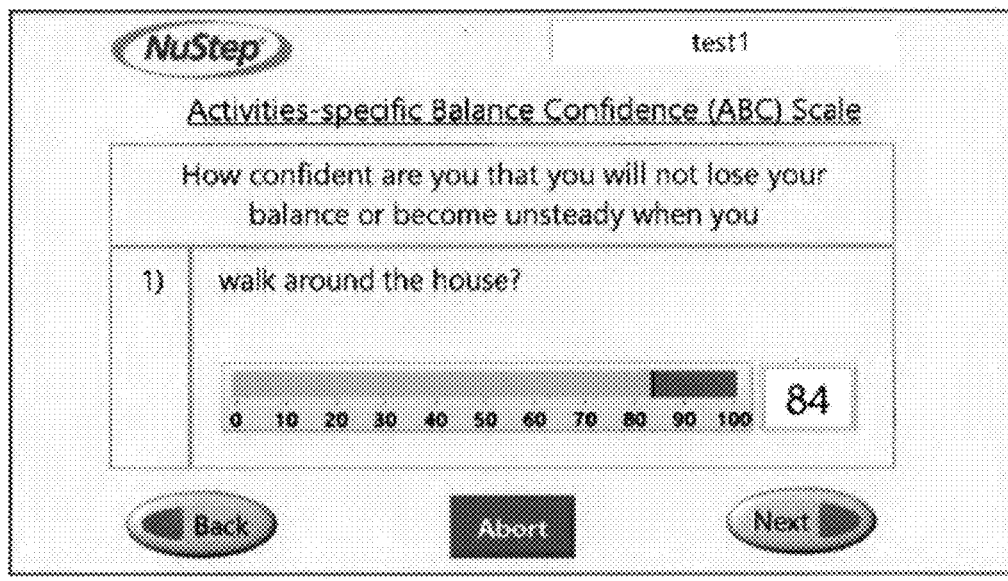

FIG. 26 is a screenshot showing a variety of various standardized tests which may be performed using the device. FIG. 27 shows a screenshot related to the Berg Balance Scale. FIGS. 28 and 29 provide screenshots related to using the device to evaluate Activities-specific Balance Confidence (ABC scale).

Figure 30:
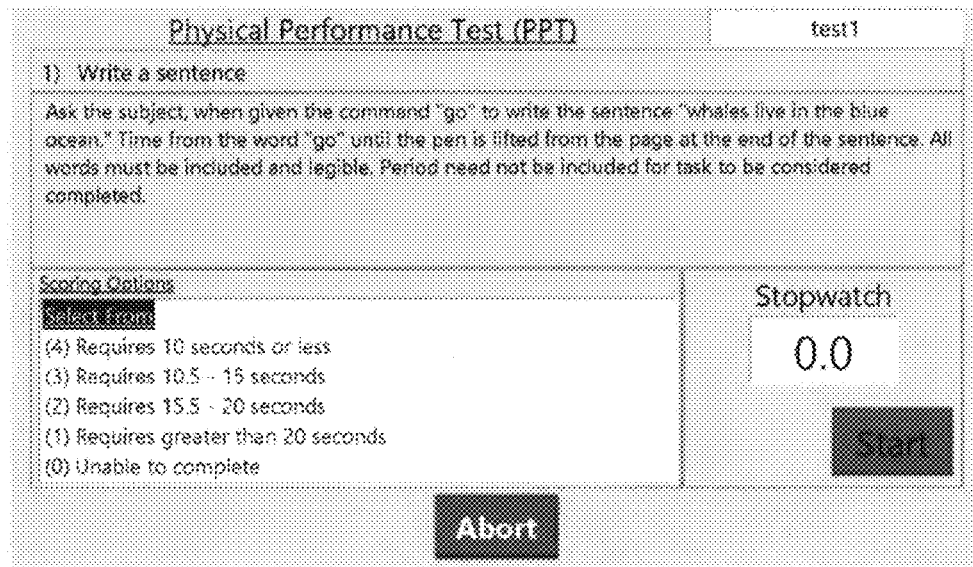
FIGS. 30 and 31 illustrate a test for using the device to perform a Physical Performance Test
Figure 31:
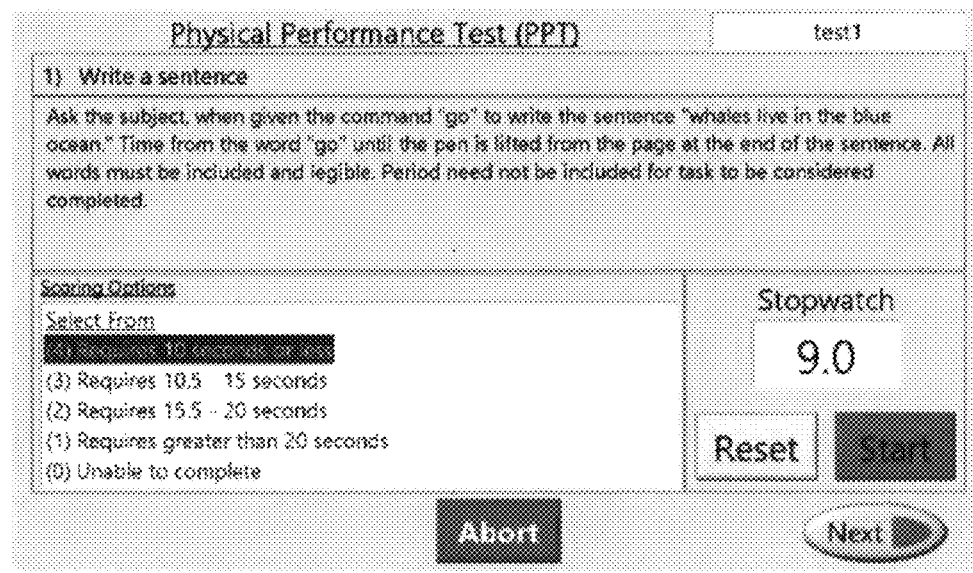
Figure 32:
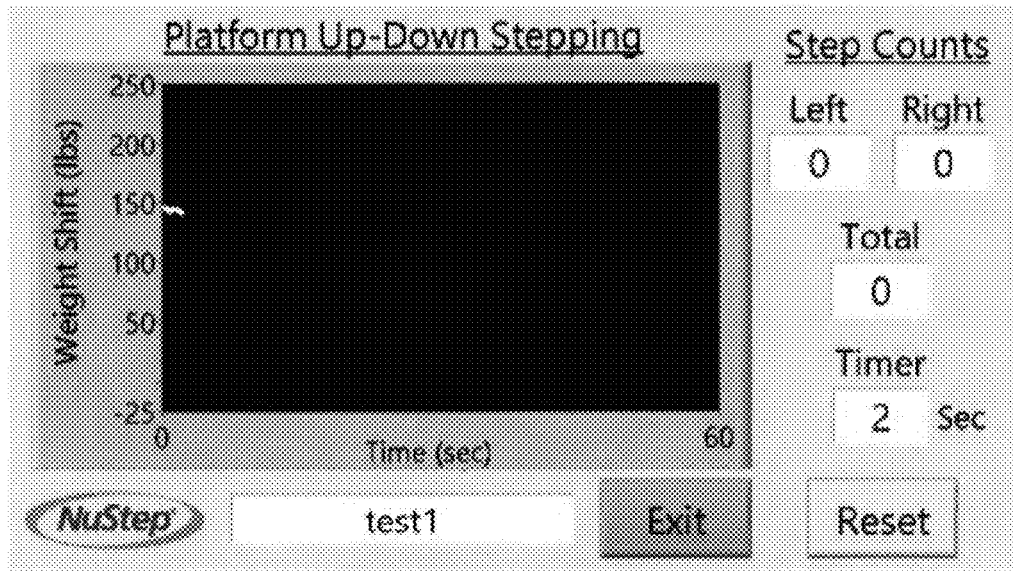
FIGS. 32 and 33 illustrate a test for using the device to perform a Platform Stepping Test
Figure 33:
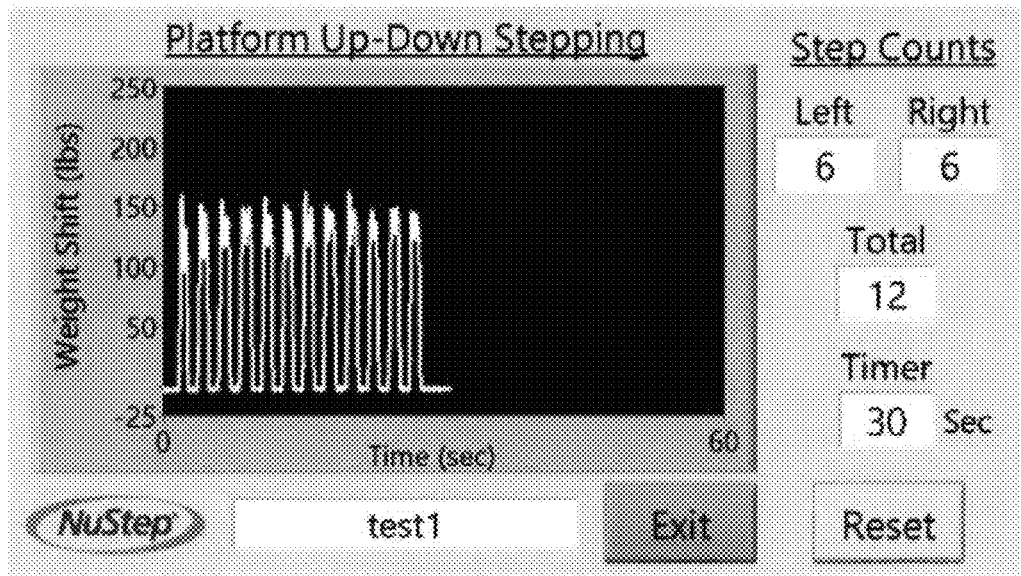

FIGS. 30 and 31 provide screenshots related to using the device to perform a Physical Performance Test (PPT). FIGS. 32 and 33 provide screenshots related to using the device to perform a Platform Stepping Test when the user steps on the stepper device 84.

Figure 34:
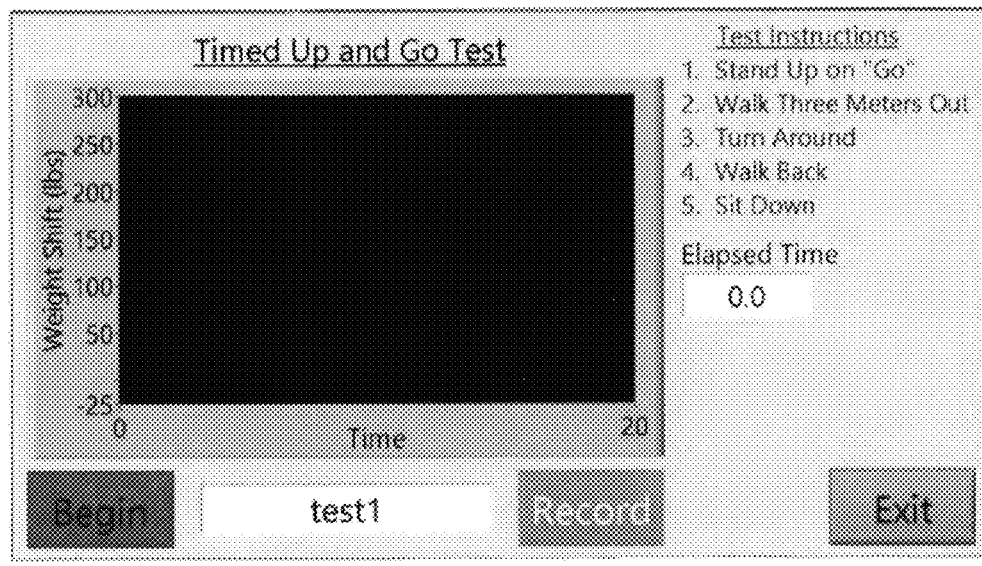
FIG. 34 illustrates a Timed Up and Go test.
Figure 35:
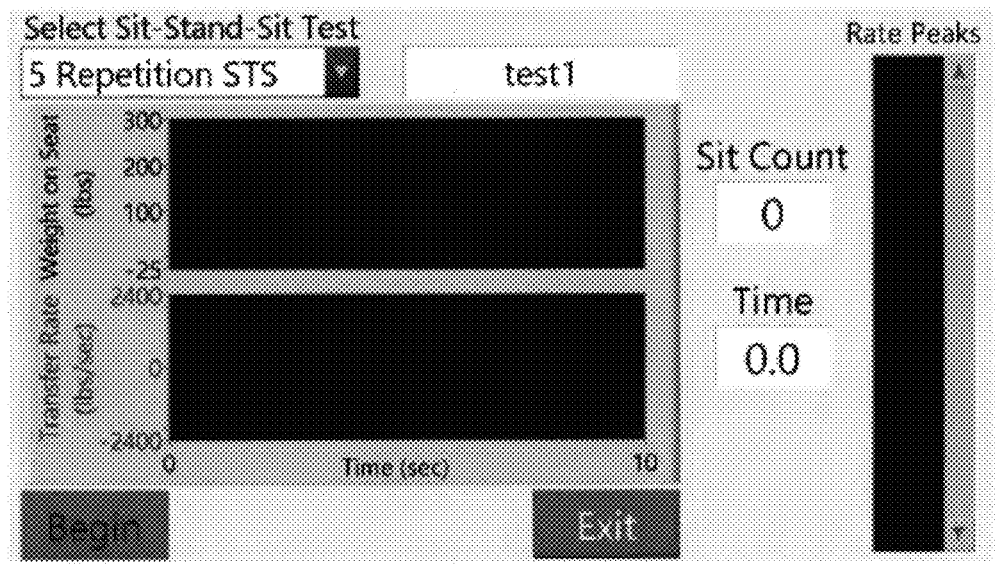
FIG. 35 illustrates performance metrics for the Sit-Stand-Sit test.

FIG. 34 provides a screenshot related using the device to perform a Timed Up and Go test. A timed up and go test provides an objective measure of the time it takes the user to stand up from a seated position, walk a set distance (for example, three meters), and sit down again. FIG. 35 provides a screenshot of a Sit-Stand-Sit test that provides an objective measure of the number and quality of the sit to stand to sit actions the user is able to perform in a preset time interval or how long it takes him or her to perform a preset number of sit-stand-sit actions. The Quality is unique to this machine as it can quantify the rate of force change as the user makes downward contact with the seat. It provides an estimate of the "plopping" impact as the user engages the seat of the device 10 and can be used to identify excessive impacts and teach users to reduce the level of potentially harmful impacts.

Figure 36:
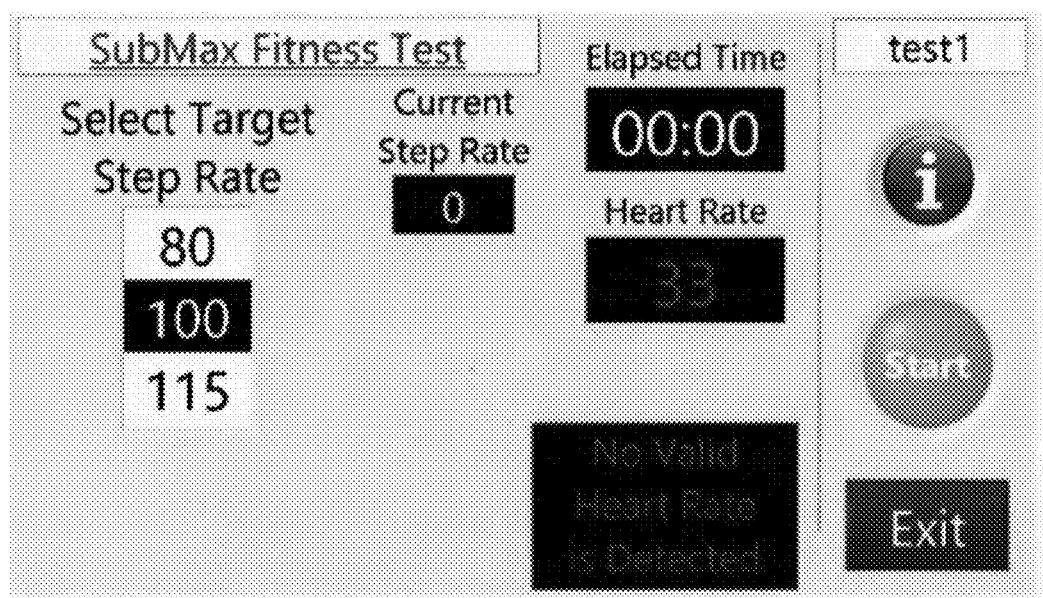
FIG. 36 illustrates an interface when using the device to perform a subMax Fitness test.

FIG. 36 provides a screenshot related to using the device to perform a subMax Fitness test when the user utilizes the pedal systems 16a and 16b, and/or handle bar systems 14a and 14b. During a sub-maximal aerobic fitness test, heart rate, age, gender, weight, and measured power output may be used to estimate VO2 max. Unlike direct VO2 max measurement, during a sub-maximal test the heart rate should not rise above a pre-determined maximum—usually 85 percent of the estimated maximal heart rate based on age.

Figure 37:
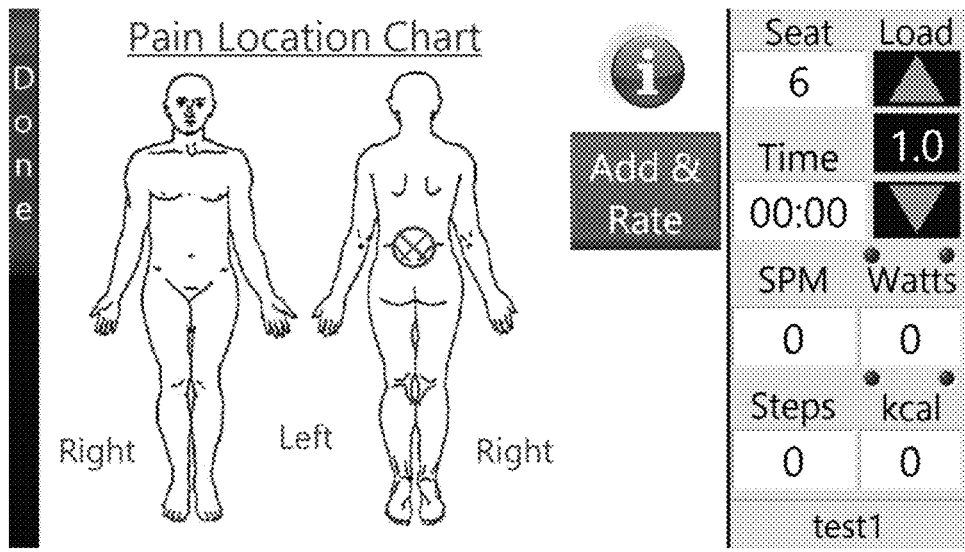
FIGS. 37 and 38 illustrate interfaces related to pain assessment.
Figure 38:
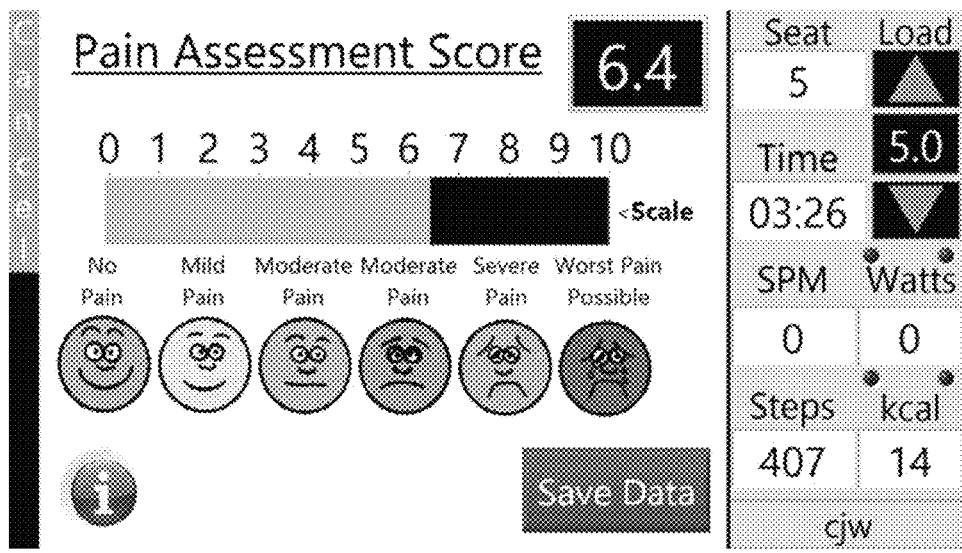
Figure 39:
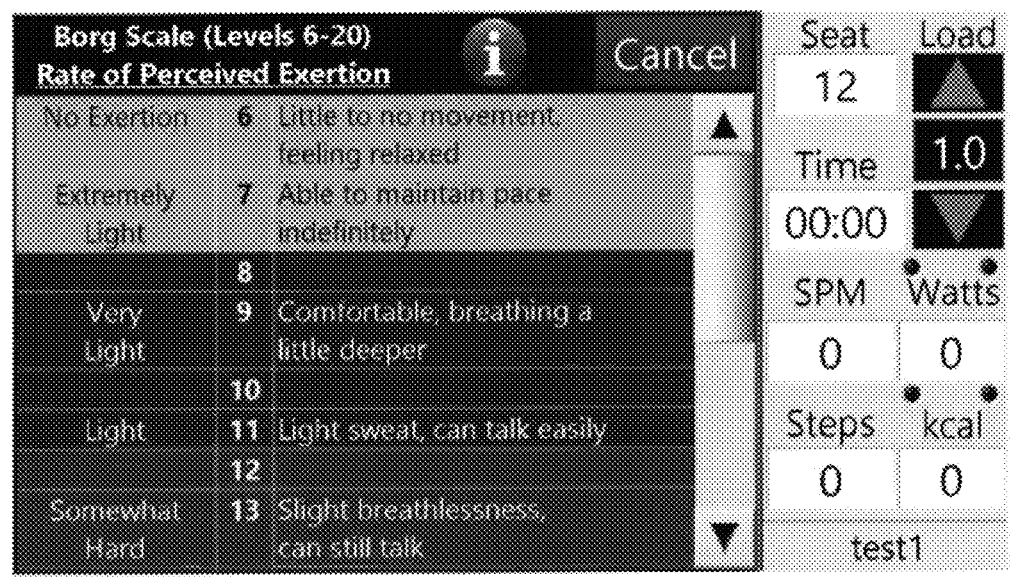
FIGS. 39-42 illustrate an interface related to a perceived exertion recording.
Figure 40:
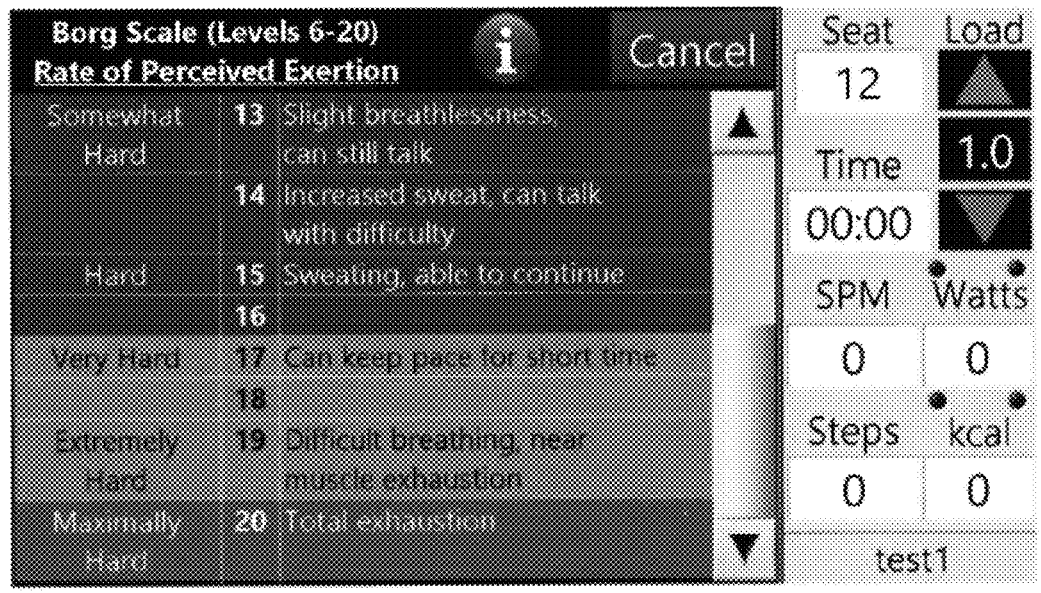
Figure 41:
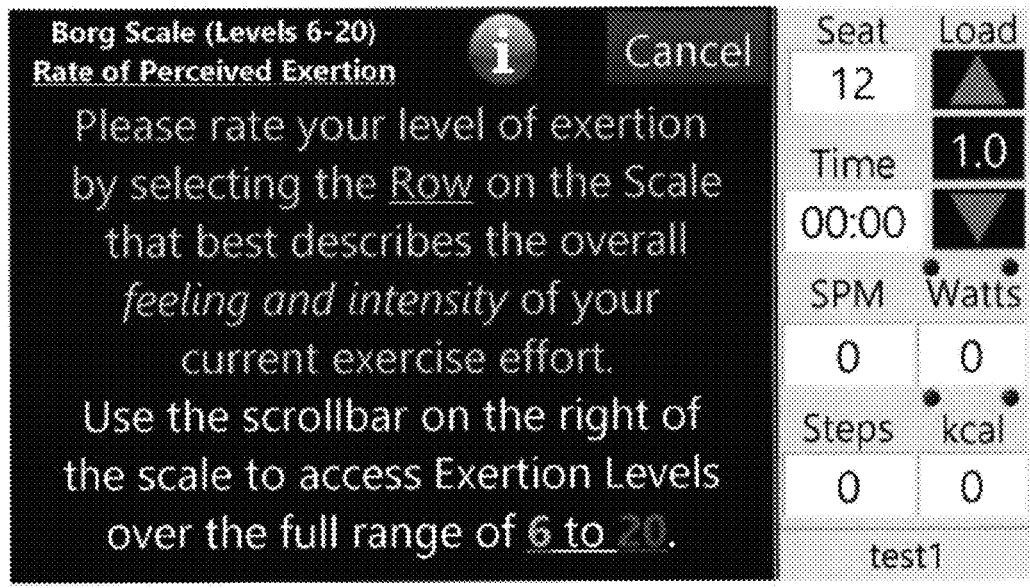
Figure 42:

FIGS. 37 and 38 provide screenshots related to pain assessment and perceived exertion screens. The pain location chart in FIG. 37 enables a user to indicate on the locations and severity of perceived pain indicated by a pain assessment score. The pain assessment score in FIG. 38 allows the user to select the pain level in the location selected by the user in FIG. 37. FIGS. 39, 40, 41, and 42 provide screenshots related to a perceived exertion recording when the user steps on the stepper device 84 or utilizes the pedal systems 16a and 16b and/or handle bar systems 14a and 14b.

Figure 43:
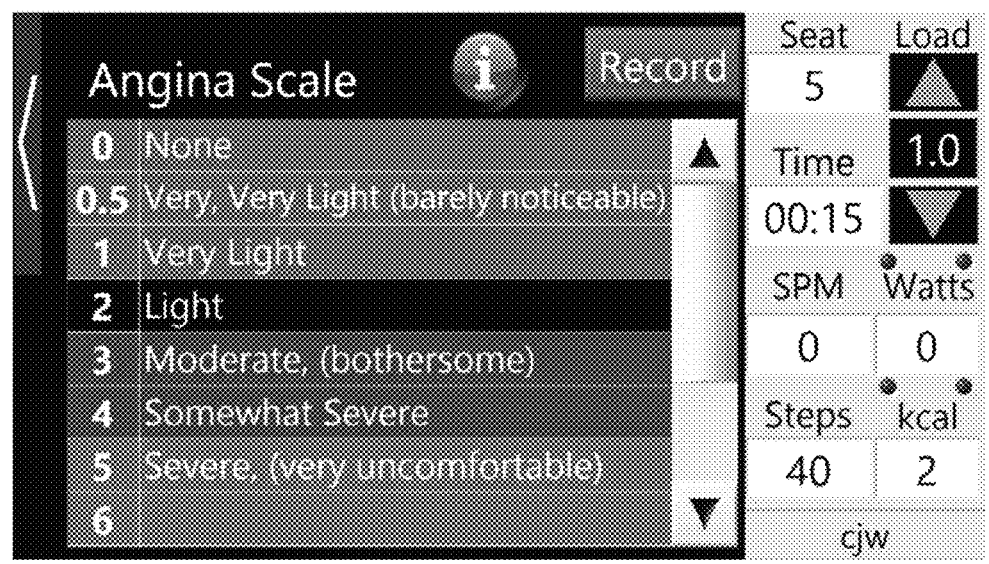
FIG. 43 illustrates an interface related to recording an angina scale.
Figure 44:
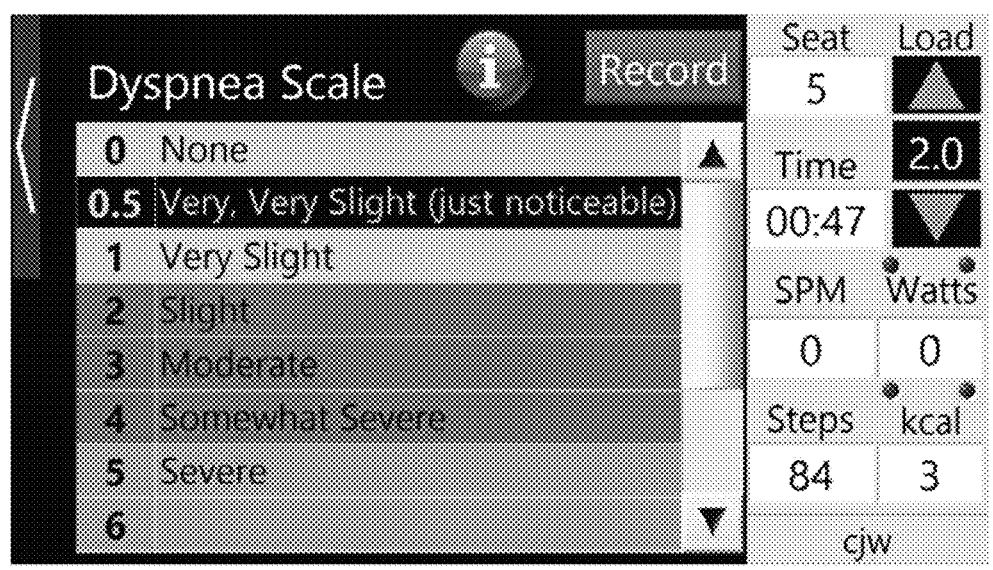
FIG. 44 illustrates an interface related to recording a dyspnea scale.

FIG. 43 shows a screenshot related to recording an angina scale when the user steps on the stepper device 84 or utilizes the pedal systems 16a and 16b and/or handle bar systems 14a and 14b. FIG. 44 shows a screenshot related to recording a dyspnea scale. Angina and dyspnea scales are subjective scores provided by the user reporting on how he/she feels. With the device 10, the user's reported score can be tied to his/her physical performance on the device 10 during and prior to the time they report their score.

Figure 45:
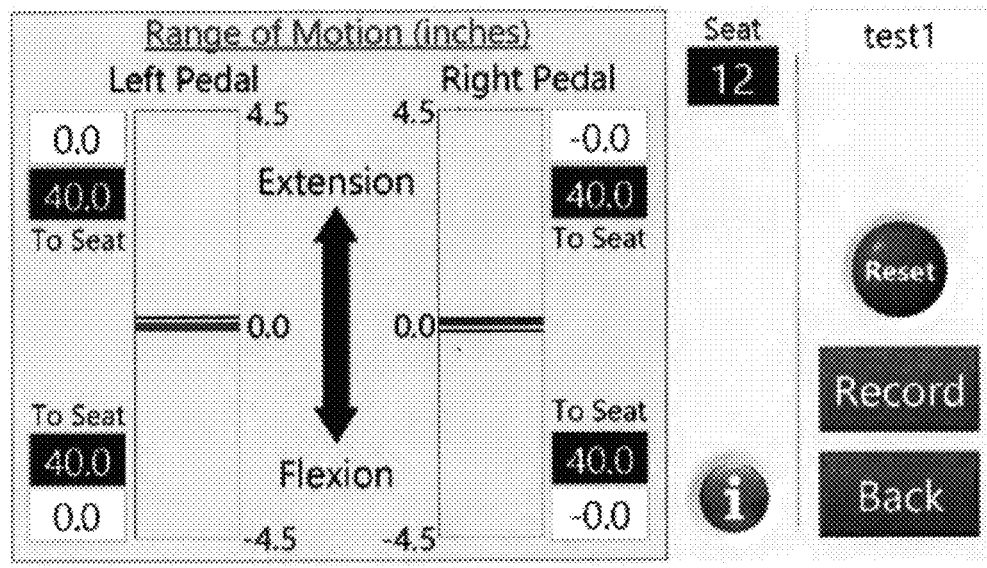
FIG. 45 illustrates an example interface related to recording of range of motion in which the ranges of motion of the left and right pedals are graphically depicted.

FIG. 45 provides a screenshot related to recording of range of motion in which the ranges of motion of the left and right pedals (relative amount of hip and knee flexion and extension as relative to the neutral position of the pedals and the position of the seat) are graphically depicted when the user utilizes the pedal systems 16a and 16b and/or handle bar systems 14a and 14b.

Figure 46:
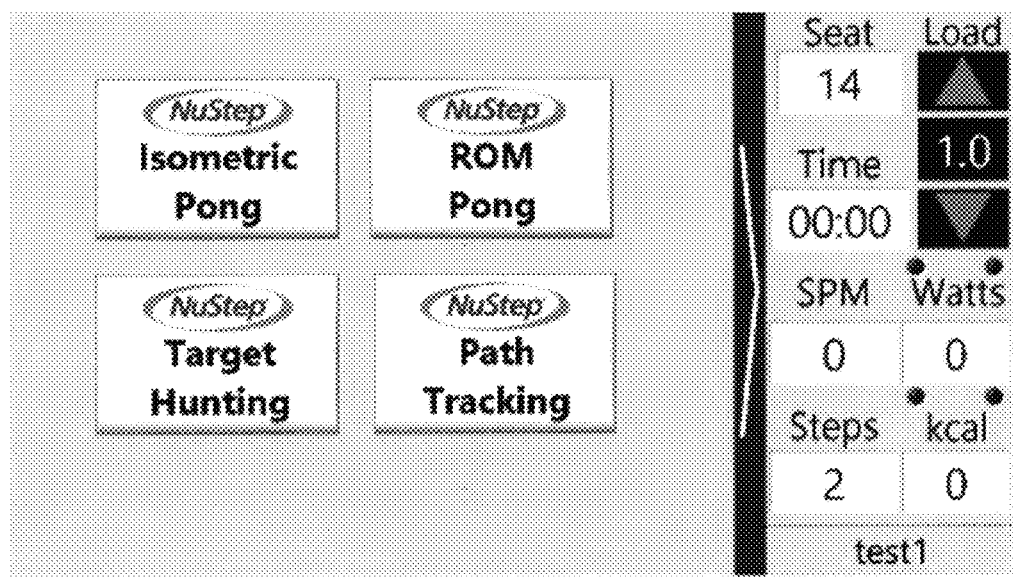
FIG. 46 illustrates an interface related to examples of games which can be played to challenge a user of the device.
Figure 47:
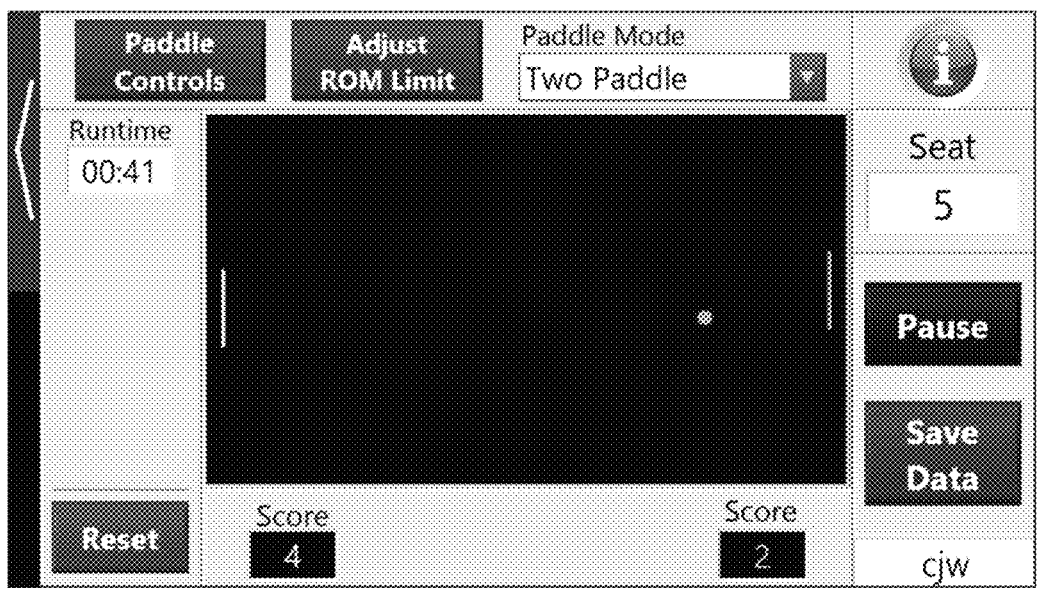
FIGS. 47 and 48 illustrate an interface showing a user playing the isometric "Pong" game.
Figure 48:
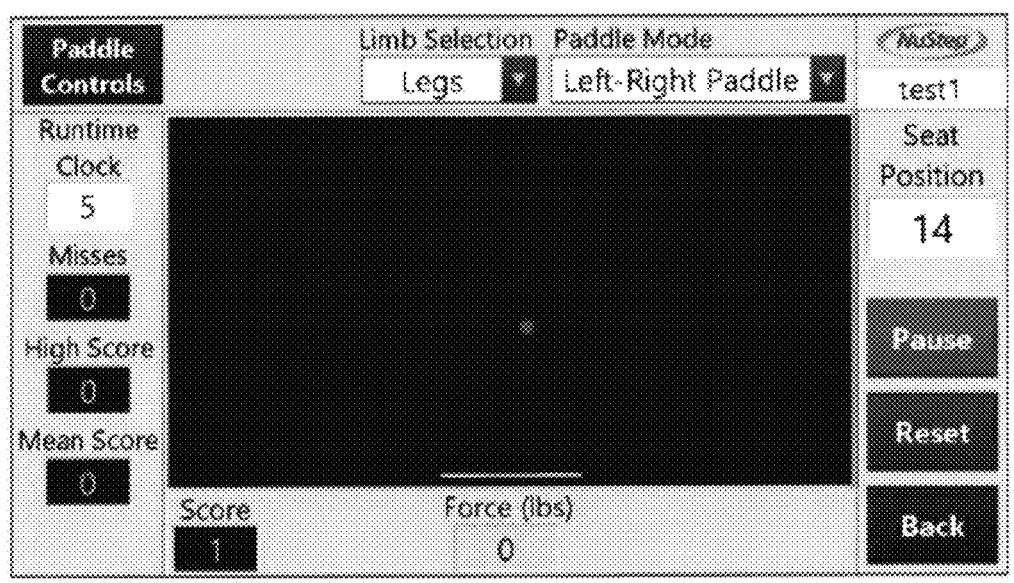

FIG. 46 provides a screenshot showing examples of games which can be played to challenge a user of the device. FIG. 47 is a screenshot showing a user playing the isometric "Pong" game when the user utilizes the pedal systems 16a and 16b and/or handle bar systems 14a and 14b. FIG. 48 provides a screenshot related to isometric Pong showing a two paddle form of the game (left leg/arm versus right leg/arm). The game can be played using force inputs when the user utilizes the pedal systems 16a and 16b and/or handle bar systems 14a and 14b.

Figure 49:
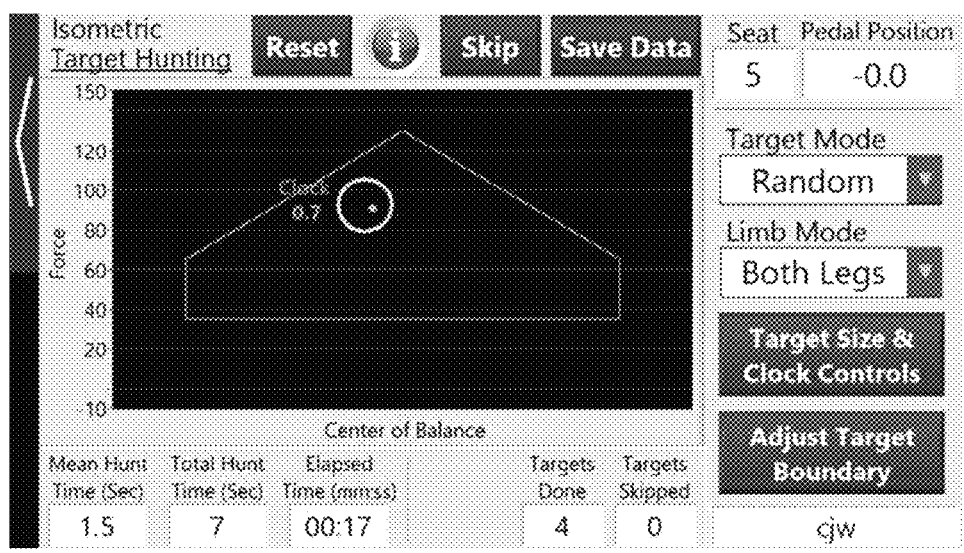
FIG. 49 illustrates an interface related to using the device to play an isometric target hunting game.

FIG. 49 is a screenshot related to using the device to play an isometric target hunting game. In this game, forces from two or more of the sensors are graphed in a coordinate plane when the user applies force to the pedal systems 16a and 16b and/or handle bar systems 14a and 14b. A point within the coordinate plane is plotted such that its left-right or x-axis location is based on the left-right balance of pressures applied to the left and right pedals or the balance of forces applied to the left and right arms. The up down-position or y-axis in the coordinate plane is determined by the total force applied to both pedals or both arms. A user is challenged with the task to locate the graphical point within a desired target circle by controlling forces applied by his or her limbs to the pedal systems 16a and 16b and/or handle bar systems 14a and 14b. The target can be stationary, moved manually by touching the screen within the coordinate plane, or moved programmatically to random, preset stock, or user programmed customized locations around the screen each time a clock timer counts to zero. The clock is reset to a predetermined value at each new position. The target circle can also move on lines or open or closed figures to enable users to play a path tracking game. The boundaries for bilateral use are displayed in a "house" shape to accommodate total force contributed by both legs: center being higher because both legs contribute equally in the center. The boundary values can be controlled via controls in the example options provided. A single leg modes may also be utilized which may be useful for ankle training.

Figure 57:
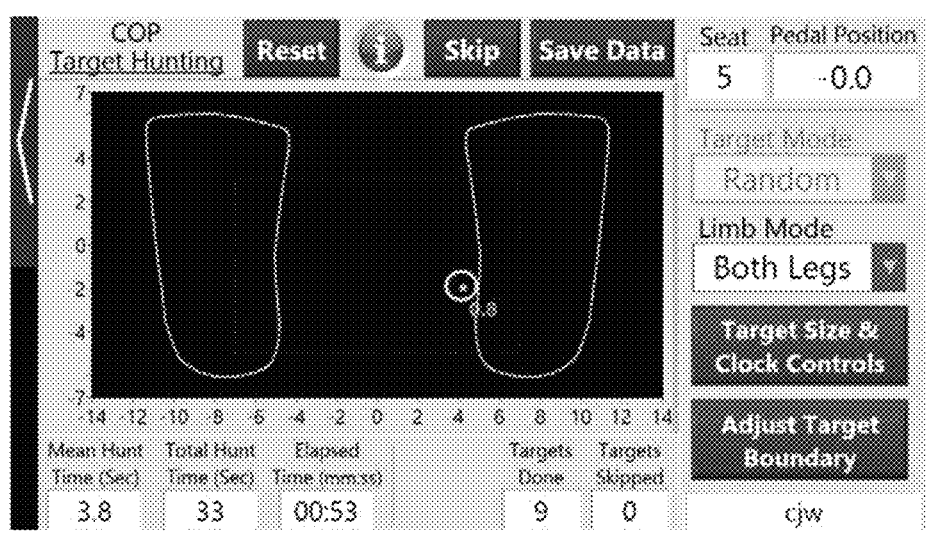
FIG. 57 illustrates an interface related to using the device to play a center of pressure target hunting game.

Additionally or alternatively, as seen in the screen shot displayed in FIG. 57, a center of pressure target hunting game restricted to the legs may be played whereby the user uses his/her feet to apply controlled forces to the pedal systems 16a and 16b such that the location of the graphical point in the coordinate plane is determined by the center of pressure applied by both feet or within the boundaries of the individual pedals for single foot use. For this game, adapting loads heel-to-toe moves the graphical point up and down in the y-axis. The object of the game is to place the center of pressure, as represented by the point, in a target circle. Single leg modes may also be utilized which may be useful for ankle training.

Figure 50:
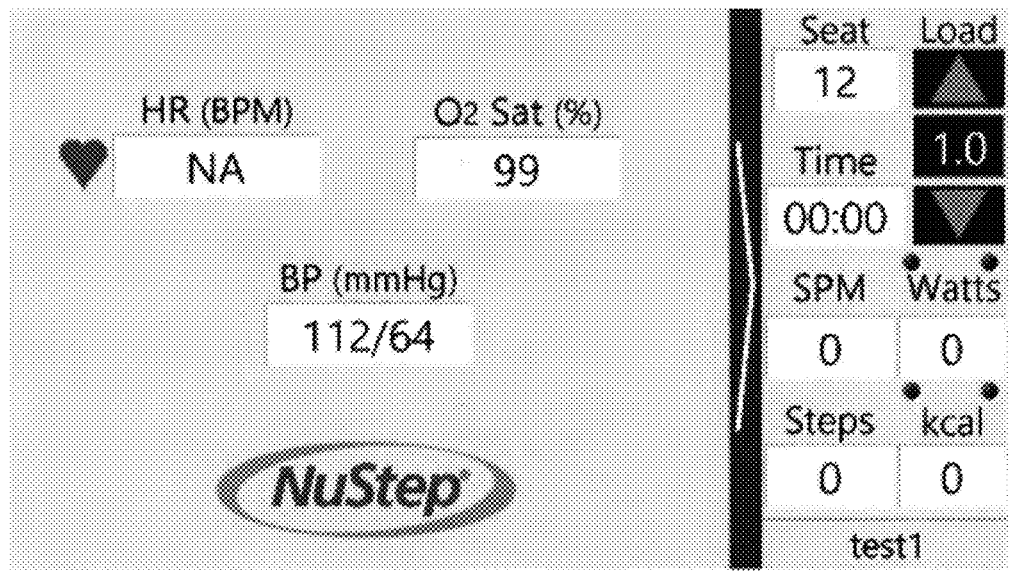
FIG. 50 illustrates an interface related to showing a display of vital signs for the user.

FIG. 50 provides a screenshot showing the display of example vital signs for the user. This information may be collected by sensors 113 to measure any one of a number of varieties of variables of the device 10 or even the user, such as biometrics of the user, including pulse rate of the user and oxygen saturation are also possible.

Figure 51:
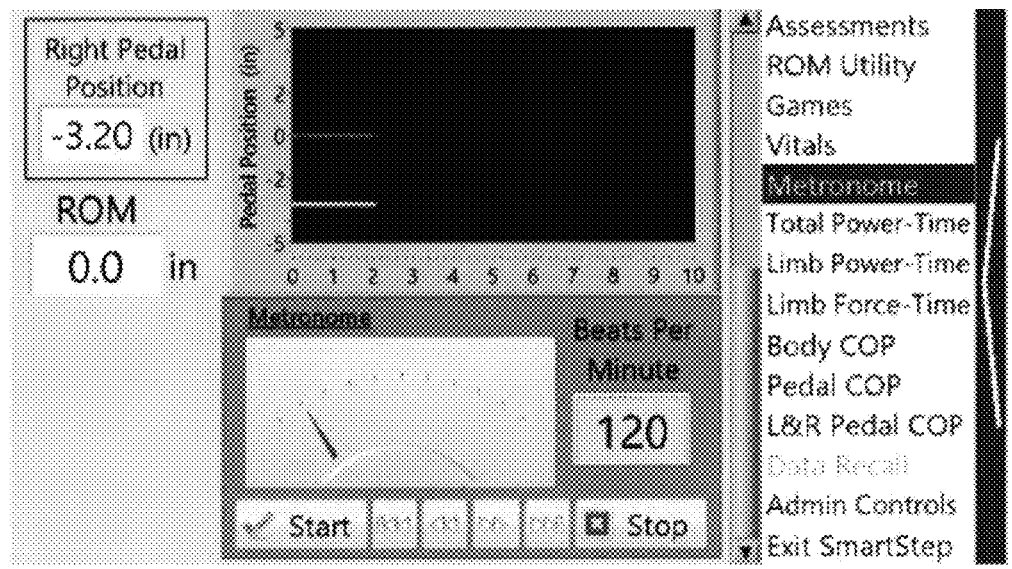
FIGS. 51-53 illustrate an interface related to a metronome for pacing the user of the device.
Figure 52:
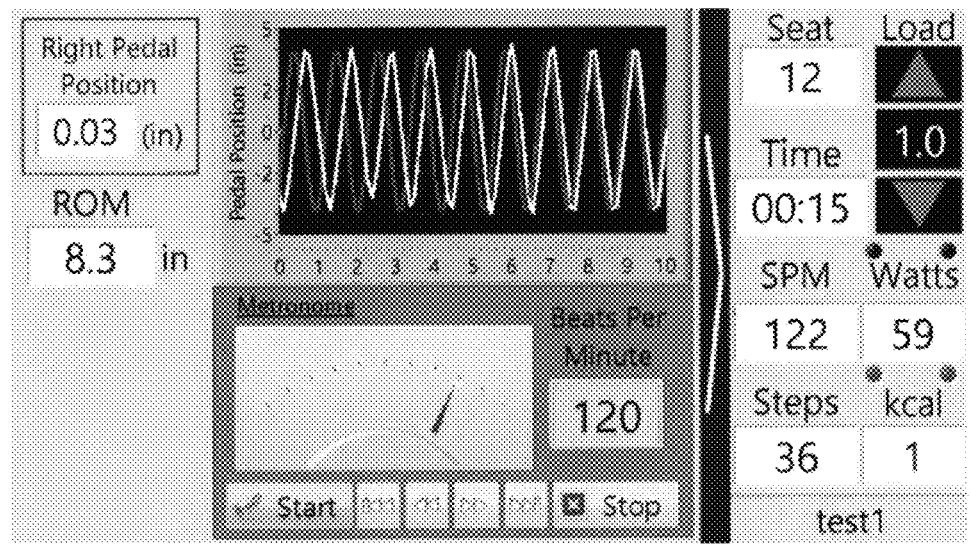
Figure 53:
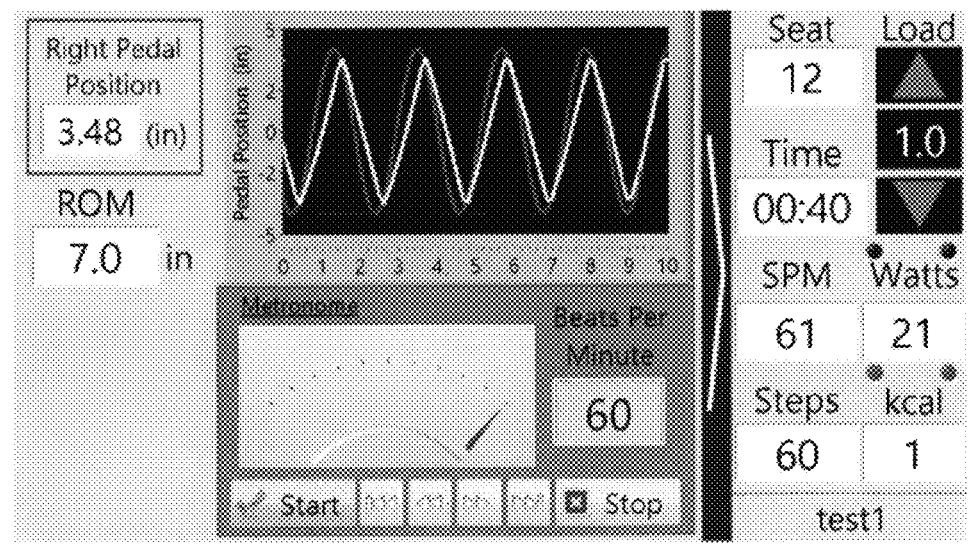

FIGS. 51, 52, and 53 provide screen shots of a metronome for cueing and pacing the user in using the device when the user utilizes the pedal systems 16a and 16b and/or handle bar systems 14a and 14b. The user draws an oscillating path on the screen via the output of the system position sensor as he or she moves the pedals and arms in a reciprocating motion. The challenge is to keep pace with the metronome and trace its oscillating path displayed on the screen. A score is calculated to provide a measure of performance accuracy. Controls are provided to enable adjustment of the metronome step rate pace and amplitude or range of motion of user steps.

Figure 54:
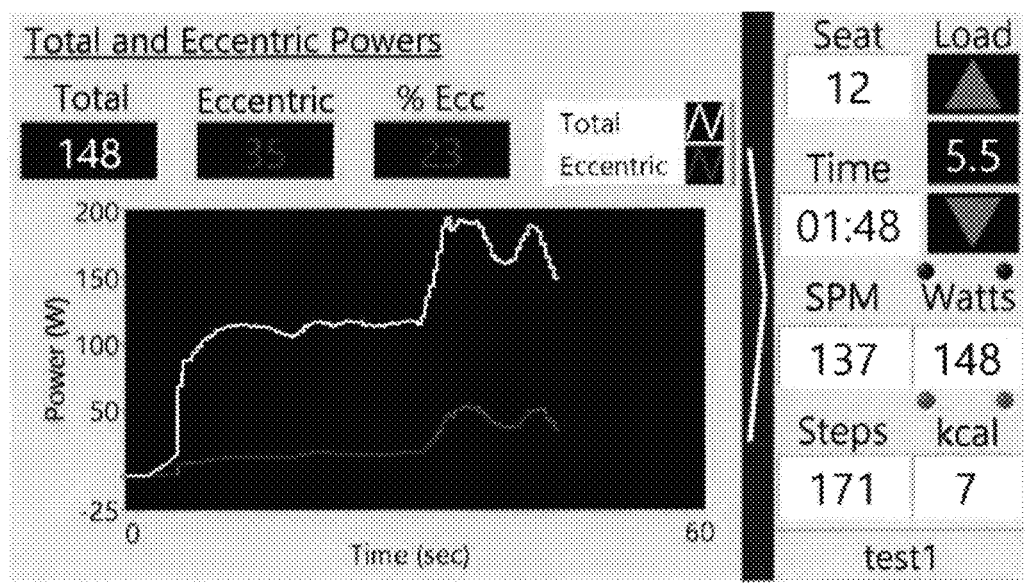
FIG. 54 illustrates an interface related to display of total and eccentric power.
Figure 55:
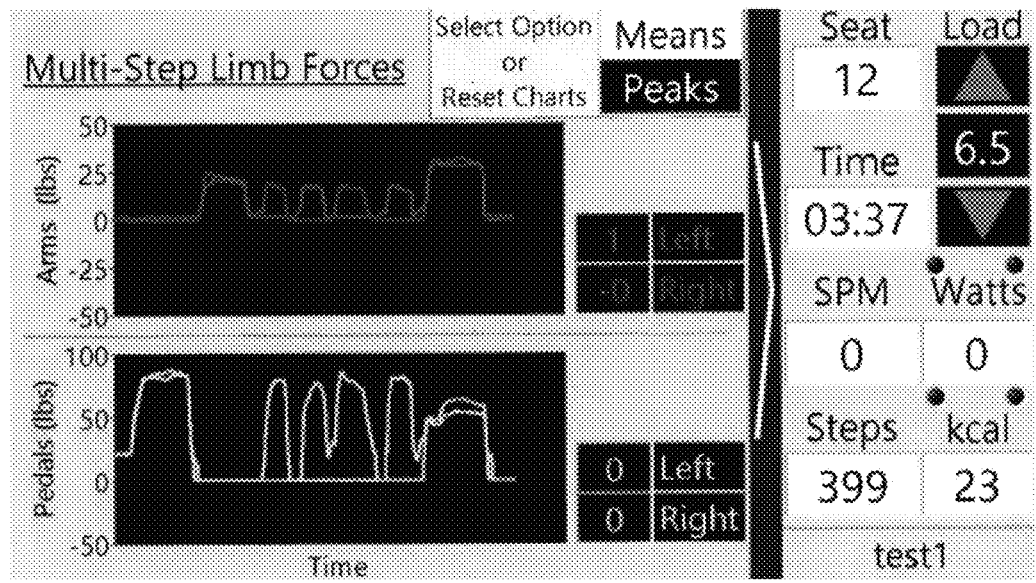
FIG. 55 illustrates an interface related to display of limb forces.

FIG. 54 provides a screenshot related to display of total and eccentric power when the user utilizes the pedal systems 16a and 16b and/or handle bar systems 14a and 14b. FIG. 55 provides a screenshot related to display of a rolling mean or peak stepping force calculated over the most recent window of a specified number of steps or time period when the user utilizes the pedal systems 16a and 16b and/or handle bar systems 14a and 14b.

Figure 56:
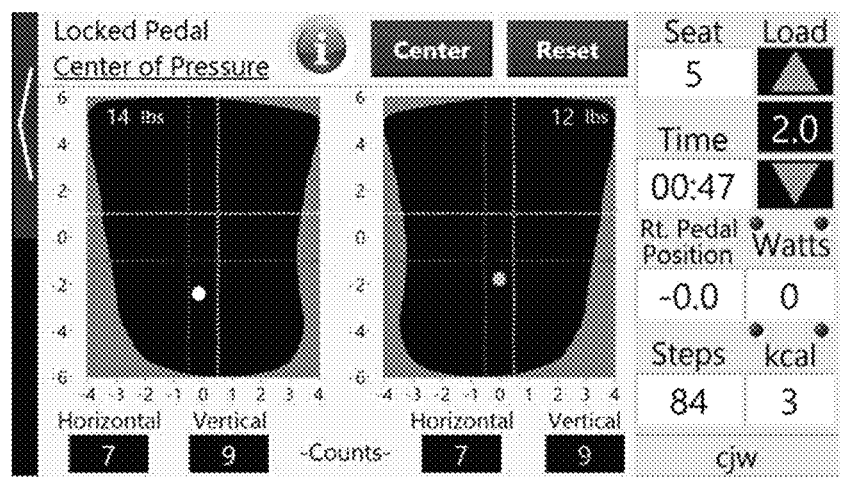
FIG. 56 illustrates an interface related to a display of the center of pressures applied to the pedals by each foot as the user is seated on the device.

FIG. 56 provides a screenshot of a display of a COP pedal game whereby the user applies pressure to the pedal systems 16a and 16b to move a point on coordinate planes, mapping each pedal surface, up and down (y-axis) and left and right (x-axis) across adjustable boundaries represented by graphical cursors. The graphical points on each graph are moved by adjusting the center of pressures applied by each individual foot. For each foot, the game increments a horizontal or vertical counter each time the center of pressure point moves across both horizontal cursors or vertical cursors, respectively. Additionally, a similar game can be played using the weight sensors whereby the center of pressure of user body weight can be mapped on a graphic. The center of pressure of user body weight can also be used to monitor a degree of body posture and seated and/or standing balance.

Figure 58:
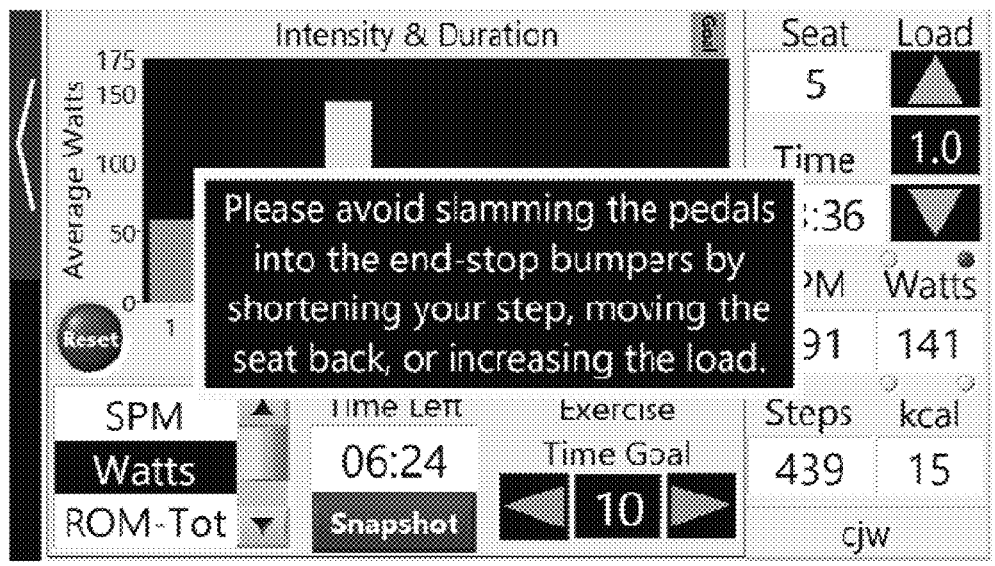
FIG. 58 illustrates an interface related to an excessively hard and repeated bumper impact warning.

FIG. 58 illustrates a screenshot of an excessively hard and repeated bumper impact warning. This monitoring runs in the background of all dynamic exercise on the system. Essentially, the position sensor 104 is used to detect the position of the handle bar systems 14a and 14b and pedal systems 16a and 16b. This information along with velocity, stepping rate, resistance load level, and other inputs is used by is the computational and data acquisition unit 110, to determine if the end stop bumpers are being impacted excessively hard. If they are, the warning shown in FIG. 58 may be displayed to the user. An intensity and duration interface is shown in the background that plots steps per minute, power output in watts, range of motion total, range of motion extension for left and right legs, range of motion flexion for left and right legs, METS or heart rate in a bar graph. Data averaged of period of time, such as a minute, are binned and plotted as bars. Multiple bars are plotted across the graph as the time of exercise progresses. A bar to the right of the averaged bins is provided in a different color show live performance.

Figure 59:
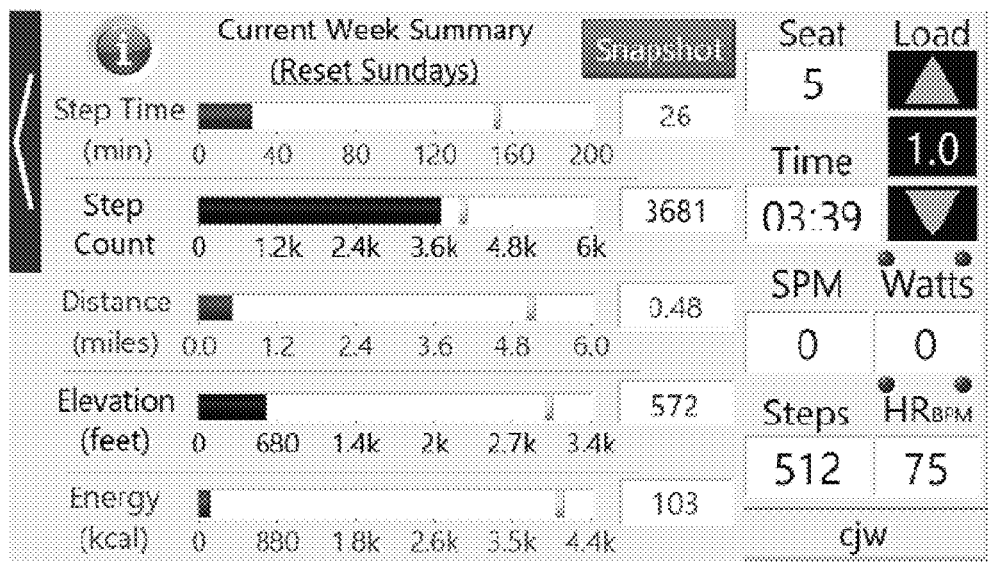
FIG. 59 illustrates an interface of a goal setting and monitoring progress screenshot.

FIG. 59 illustrates an example screenshot of goal setting and monitoring progress toward those goals. These goals are general weekly goals. For example, these goals may include step time, step count, distance, elevation and/or energy expended.

Figure 60:
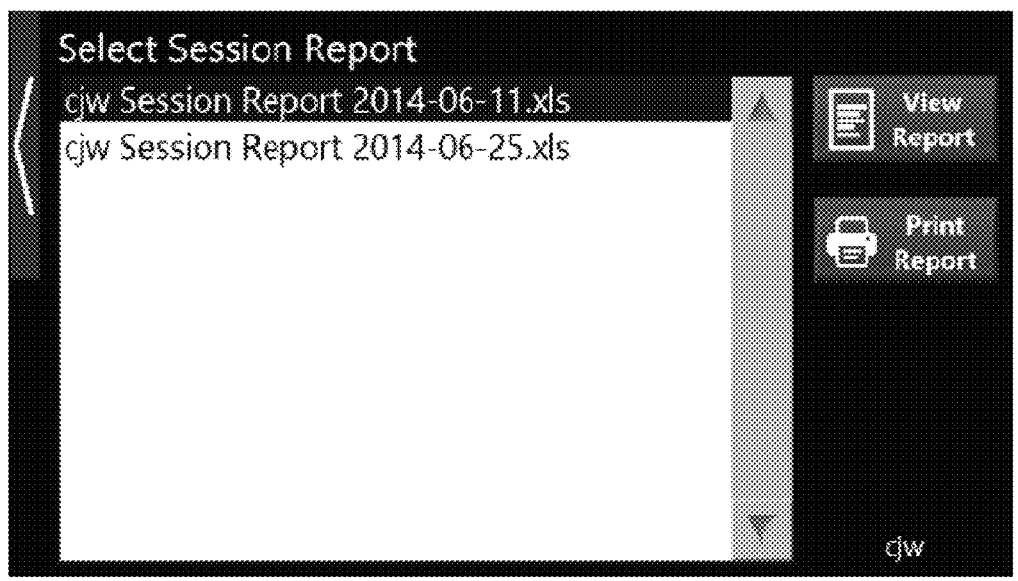
FIG. 60 illustrates an interface of a menu of performance reports.

FIG. 60 illustrates an example of a recall feature. Here, the user can view and print user-specific and time stamped session, test, and performance reports.

Figure 61:
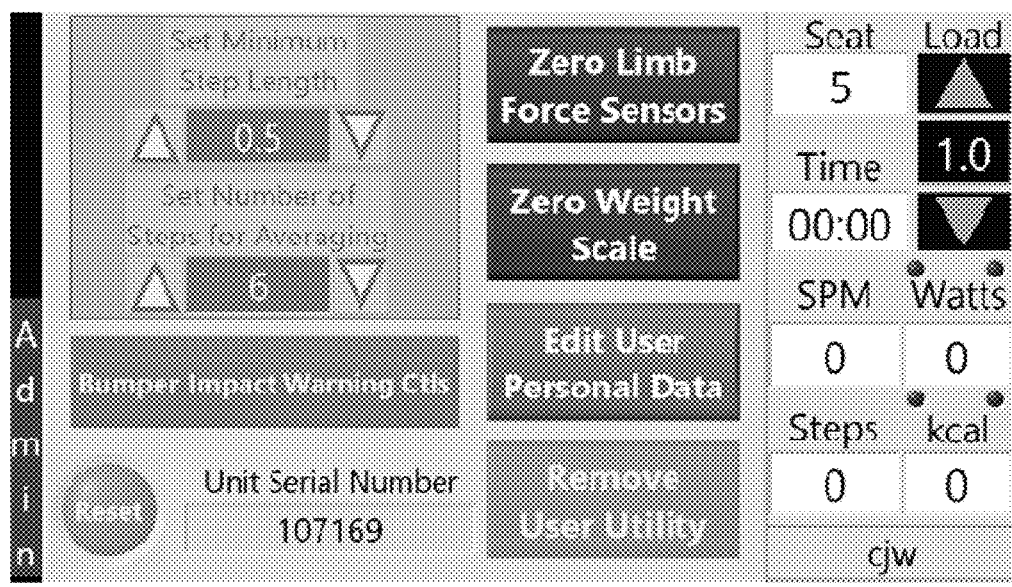
FIG. 61 illustrates an interface of an administration menu page.

FIG. 61 illustrates an example administration page. Here, the user can select menu options to zero the limb force sensors or weight scale, set minimum step length for step counting and step rate calculations, as well as edit personal data, such as weight, height, etc. More specifically, the computational and data acquisition unit 110 may be configured to count steps based on a minimum step length setting, and calculate step rate and velocity of movement.

FIG. 62 illustrates an example of a main menu page. Here, the user applications are sorted into meaningful and quick to locate category menu buttons. For example, the applications may be arranged by the categories of cardio, exercise tolerance, motor control, range of motion, and strength. Further, a user can access the user's history as well as subjective scales.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

The invention claimed is:

1. A physical exercise device providing a stepper like motion for a user comprising:
    a pair of foot pedals provided for engagement by the user while seated on a seat,
    a drive train providing cyclical counter motion between the foot pedals,
    a drive train lock mechanism enabling the pedals to be locked in a locked state at a desired position along their range of motion, and enabling the pedals to be moved in an unlocked state,
    a position sensor for providing position signals of the pedals, wherein the pedals move over a range of motion,
    pedal force plates for measuring forces exerted by the user on each of the pedals and providing pedal force signals,
    a computational and data acquisition unit for receiving the position signal and the pedal force signals and recording the pedal force signals over the position of the drive train and enabling computation of performance of the user in dynamic activity with the drive train lock mechanism in the unlocked state, and enabling computation of performance of the user in static activity with the drive train lock mechanism in the locked state, and
    a user interface system incorporating a user interface screen enabling the user to receive information regarding the dynamic and the static activity.

2. The physical exercise device in accordance with claim 1, wherein the computational unit is configured to:
    count steps based on a minimum step length setting and calculate step rate and velocity of movement.

3. The physical exercise device in accordance with claim 1, wherein the computation unit configured for carrying out one or more of the following:
    measure of power expenditure by the user in the dynamic activity,
    identify power output and energy exerted by the user through each of the pedals in the dynamic activity, and
    identifying force exerted by the user at the pedals in the static activity or the dynamic activity.

4. The physical exercise device in accordance with claim 1, further comprising the computation unit being configured for displaying through the user interface biofeedback graphics for the user and enabling data input by the user.

5. The physical exercise device in accordance with claim 1, further comprising the computation unit for carrying out one or more of the following activities: a pace partner race, a progressive load test and heart rate recovery test, a muscle endurance test, a balanced power and work output application, an exercise intensity histogram, a climbing application, a maximum force test, a force limiting graphical warning, a Berg balance test, a balance ABC score, a physical performance test, a force versus time isometric training, and a subMax fitness test.

6. The physical exercise device in accordance with claim 1, further comprising the computation unit for recording at least one of, a pain assessment score, a perceived exertion scale, an angina scale, a claudication scale, and a dyspnea scale.

7. The physical exercise device in accordance with claim 1, further comprising the computation unit configured for enabling games to be played including one or more of, a force control target hunting, center of pressure pedal target hunting, center of pressure pedal, a force control path tracking, an isometric Pong, and a range of motion Pong.

8. The physical exercise device in accordance with claim 1, further comprising computation unit for providing at least one of a metronome, a power graphic for each pedal, and a center of pressure graphic.

9. The physical exercise device in accordance with claim 1, further comprising the seat being a movable in a fore and aft direction, and a seat position transducer for detecting the position of the seat and providing a seat position signal for the computational unit, the computational and data acquisition unit recording the seat position signal.

10. The physical exercise device in accordance with claim 1, further comprising use of the device for exercise of the user.

11. The physical exercise device in accordance with claim 1, further comprising use of the device for rehabilitation of the user.

12. The physical exercise device in accordance with claim 1, further comprising use of the device for training of the user.

13. The physical exercise device in accordance with claim 1, further comprising use of the device for physical therapy of the user.

14. A physical exercise device in accordance with claim 1 further comprising use of the device for physiological assessment of the user.

15. A physical exercise device providing a stepper like motion for a user comprising:
    a pair of foot pedals provided for engagement by the user while seated on a seat,
    a pair of arms provided for grasping by the user while seated on the seat,
    a drive train providing contralateral motion between the pair of arms and the pair of foot pedals,
    a pedal and arm lock mechanism enabling the pedals and the arms to be locked in a locked state at a desired position along their range of motion, and enabling the arms and the pedals to be moved in an unlocked state,
    a position sensor for providing signals related to the position of the arms and the foot pedals,
    pedal force plates for measuring forces exerted by the user on each of the pedals,
    arm force sensors for measuring force applied to each arm by the user,
    a computational and data acquisition unit for receiving the position signal and the pedal force signals and arm force signals and recording the pedal force signals and arm force signals over the range of motion of the drive train and enabling computation of performance of the user in dynamic activity with the drive train lock mechanism in the unlocked state, and static activity with the drive train lock mechanism in the locked state, and a user interface system incorporating a user interface screen.

16. The physical exercise device in accordance with claim 15, wherein the computational unit is configured to:
count steps based on a minimum step length setting; and
calculate step rate and velocity of movement.

17. The physical exercise device in accordance with claim 15, wherein the computation unit configured for carrying out one or more of the following:
measure of power expenditure by the user in the dynamic activity,
identify power output and energy exerted by the user through each of the pedals or arms in the dynamic activity, and
identifying force exerted by the user at the pedals or arms in the static activity or the dynamic activity.

18. The physical exercise device in accordance with claim 15, further comprising the computation unit being configured for displaying through the user interface biofeedback graphics for the user and enabling data input by the user.

19. The physical exercise device in accordance with claim 15, further comprising the computation unit for carrying out one or more of the following activities: a pace partner, a progressive load test and heart rate recovery test, a muscle endurance test, a balanced power and work output application, an exercise intensity histogram, a climbing application, a maximum force test, a force limiting graphical warning, a Berg balance test, a balance ABC score, a physical performance test, a force versus time isometric training, and a subMax fitness test.

20. The physical exercise device in accordance with claim 15, further comprising the computation unit for recording at least one of, a pain assessment score, a perceived exertion scale, an angina scale, a claudication scale, and a dyspnea scale.

21. The physical exercise device in accordance with claim 15, further comprising the computation unit configured for enabling games to be played including one or more of, a force control target hunting, center of pressure target hunting, center of pressure pedal, a force control path tracking, an isometric Pong, and a range of motion Pong.

22. The physical exercise device in accordance with claim 15, further comprising computation unit for providing at least one of a metronome, a power graphic for each pedal or arm, and a center of pressure graphic.

23. The physical exercise device in accordance with claim 15, further comprising the seat being a movable in a fore and aft direction, and a seat position transducer for detecting the position of the seat and providing a seat position signal for the computational unit, the computational and data acquisition unit recording the seat position signal.

24. The physical exercise device in accordance with claim 15, further comprising use of the device for exercise of the user.

25. The physical exercise device in accordance with claim 15, further comprising use of the device for rehabilitation of the user.

26. The physical exercise device in accordance with claim 15, further comprising use of the device for training of the user.

27. The physical exercise device in accordance with claim 15, further comprising use of the device for physical therapy of the user.

28. The physical exercise device in accordance with claim 15, further comprising use of the device for physiological assessment of the user.

29. The physical exercise device in accordance with claim 15, further comprising:
an arm measuring sensor for measuring a telescoped length of each arm, the telescoped length of each arm substantially being a distance the handle is telescoped and locked from a pivot point of a base of the arm; and
wherein the computational and data acquisition unit is configured to record the arm length signal.

30. A physical exercise device providing a stepper like motion for a user comprising:
a pair of foot pedals provided for engagement by the user while seated on a seat,
a pair of arms provided for grasping by the user while seated on the seat,
a drive train providing contralateral motion between the pair of arms and the pair of foot pedals,
a pedal and arm lock mechanism enabling the pedals and the arms to be locked in a locked state at a desired position along their range of motion, and enabling the arms and the pedals to be moved in an unlocked state,
a position sensor for providing signals related to the position of the arms and the foot pedals,
pedal force plates for measuring forces exerted by the user on each of the pedals,
arm force sensors for measuring force applied to each arm by the user,
sensors for measuring weight of the device on the ground,
a computational and data acquisition unit for receiving the position signal and the pedal force signals and arm force signals and weight signals and recording the pedal force signals and arm force signals and weight signals over the range of motion of the drive train and enabling computation of performance of the user in dynamic activity with the drive train lock mechanism in the unlocked state, and static activity with the drive train lock mechanism in the locked state, and
a user interface system incorporating a user interface screen.

31. The physical exercise device in accordance with claim 30, wherein the computational unit is configured to:
count steps based on a minimum step length setting; and
calculate step rate and velocity of movement.

32. The physical exercise device in accordance with claim 30, wherein the computation unit configured for carrying out one or more of the following:
measure of power expenditure by the user in the dynamic activity,
identify power output and energy exerted by the user through each of the pedals or arms in the dynamic activity,
identifying force exerted by the user at the pedals or arms in the static activity or the dynamic activity, and
measure of user body weight.

33. The physical exercise device in accordance with claim 30, further comprising the computation unit being configured for displaying through the user interface biofeedback graphics for the user and enabling data input by the user.

34. The physical exercise device in accordance with claim 30, further comprising the computation unit for carrying out one or more of the following activities: a pace partner exercise, a progressive load test and heart rate recovery test, a muscle endurance test, a balanced power and work output application, an exercise intensity histogram, a climbing application, a maximum force test, a force limiting graphical warning, a platform up-down stepping application, a timed-up and go test, a sit to stand or sit-stand-sit test, a Berg balance test, a balance ABC score, a physical performance test, a force versus time isometric training, and a subMax fitness test.

35. The physical exercise device in accordance with claim 30, further comprising the computation unit for recording at least one of, a pain assessment score, a perceived exertion scale, an angina scale, a claudication scale, and a dyspnea scale.

36. The physical exercise device in accordance with claim 30, further comprising the computation unit configured for enabling games to be played including one or more of, a force control target hunting, center of pressure target hunting, center of pressure pedal, a force control path tracking, an isometric Pong, and a range of motion Pong.

37. The physical exercise device in accordance with claim 30, further comprising computation unit for providing at least one of a metronome, a power graphic for each pedal or arm, a force graphic for each pedal or arm, a center of pressure graphic for each pedal, and a center of pressure graphic for user body weight.

38. The physical exercise device in accordance with claim 30, further comprising the seat being a movable in a fore and aft direction, and a seat position transducer for detecting the position of the seat and providing a seat position signal to the computational and data acquisition unit for recording the seat position signal.

39. The physical exercise device in accordance with claim 30, further comprising use of the device for exercise of the user.

40. The physical exercise device in accordance with claim 30, further comprising use of the device for rehabilitation of the user.

41. The physical exercise device in accordance with claim 30, further comprising use of the device for training of the user.

42. The physical exercise device in accordance with claim 30, further comprising use of the device for physical therapy of the user.

43. A physical exercise device in accordance with claim 30, further comprising use of the device for physiological assessment of the user.

* * * * *